United States Patent
Chattaraj et al.

(10) Patent No.: US 9,265,890 B2
(45) Date of Patent: Feb. 23, 2016

(54) SYRINGE PISTON WITH FINNED SEALING COVER

(75) Inventors: Sarnath Chattaraj, Simi Valley, CA (US); Poonam S. Gulati, La Canada, CA (US); Kiem Dang, Thousand Oaks, CA (US); Jocelyn Anne Montebon, Valencia, CA (US)

(73) Assignee: Medtronic MiniMed, Inc., Northridge, CA (US)

(*) Notice: Subject to any disclaimer, the term of this patent is extended or adjusted under 35 U.S.C. 154(b) by 409 days.

(21) Appl. No.: 13/415,740

(22) Filed: Mar. 8, 2012

(65) Prior Publication Data

US 2012/0165755 A1    Jun. 28, 2012

Related U.S. Application Data

(63) Continuation-in-part of application No. 12/972,263, filed on Dec. 17, 2010, now Pat. No. 8,574,201.

(60) Provisional application No. 61/289,243, filed on Dec. 22, 2009.

(51) Int. Cl.
*A61M 5/315* (2006.01)

(52) U.S. Cl.
CPC ....... *A61M 5/31511* (2013.01); *A61M 5/31513* (2013.01)

(58) Field of Classification Search
CPC ............... A61M 5/31513; A61M 2005/31521

USPC ................... 604/218, 220, 222, 192; 220/270
See application file for complete search history.

(56) References Cited

U.S. PATENT DOCUMENTS

| | | | | |
|---|---|---|---|---|
| 3,150,801 | A * | 9/1964 | Hamilton | 222/158 |
| 4,632,672 | A | 12/1986 | Kvitrud | |
| 5,314,415 | A | 5/1994 | Liebert et al. | |
| 6,723,074 | B1 * | 4/2004 | Halseth | 604/201 |
| 2007/0000951 | A1 | 1/2007 | Springhom | |
| 2007/0060896 | A1 * | 3/2007 | Miller et al. | 604/222 |
| 2007/0233002 | A1 * | 10/2007 | Cude | 604/131 |

FOREIGN PATENT DOCUMENTS

EP    0242956 A1    10/1987

* cited by examiner

*Primary Examiner* — Laura Bouchelle
(74) *Attorney, Agent, or Firm* — Ingrassia Fisher & Lorenz, P.C.

(57) ABSTRACT

Syringe pistons for a fluid syringe, and related sealing elements, are presented here. A syringe piston includes a piston body having a fluid end, an actuator end, and an outer seal-retaining surface between the fluid end and the actuator end. The syringe piston may utilize a piston sealing sleeve or a piston sealing cover. The sleeve can be coupled to the piston body around the outer seal-retaining surface, the piston sealing sleeve having a fin-shaped fluid seal element to form an interference fluid seal with an interior wall of a syringe barrel. The sealing cover can be coupled overlying the tip of the piston body. The cover has a fin-shaped fluid seal element to form an interference fluid seal with an interior wall of a syringe barrel.

20 Claims, 16 Drawing Sheets

SYRINGE PISTON WITH FINNED SEALING COVER

CROSS-REFERENCE TO RELATED APPLICATIONS

This application is a continuation-in-part of U.S. patent application Ser. No. 12/972,263, filed Dec. 17, 2010, which claims the benefit of United States provisional patent application serial number 61/289,243, filed Dec. 22, 2009.

TECHNICAL FIELD

Embodiments of the subject matter described herein relate generally to syringes and syringe pistons of the type used to deliver fluids, such as medication. More particularly, embodiments of the subject matter relate to seal configurations for a syringe piston.

BACKGROUND

Portable medical devices are useful for patients that have conditions that must be monitored on a continuous or frequent basis. For example, diabetics are usually required to modify and monitor their daily lifestyle to keep their body in balance, in particular, their blood glucose (BG) levels. Individuals with Type 1 diabetes and some individuals with Type 2 diabetes use insulin to control their BG levels. To do so, diabetics routinely keep strict schedules, including ingesting timely nutritious meals, partaking in exercise, monitoring BG levels daily, and adjusting and administering insulin dosages accordingly.

The prior art includes a number of fluid infusion devices and insulin pump systems that are designed to deliver accurate and measured doses of insulin via infusion sets (an infusion set delivers the insulin through a small diameter tube that terminates at, e.g., a cannula inserted under the patient's skin) In lieu of a traditional syringe, the patient can simply activate the insulin pump to administer an insulin bolus as needed, for example, in response to the patient's current BG level.

A typical infusion pump includes a housing, which encloses a pump drive system, a fluid containment assembly, an electronics system, and a power supply. The pump drive system typically includes a small motor (DC, stepper, solenoid, or other varieties) and drive train components such as gears, screws, and levers that convert rotational motor motion to a translational displacement of a piston in a reservoir, which may be in the form of a user-filled syringe or a pre-filled syringe. The fluid containment assembly typically includes the reservoir with the piston, tubing, and a catheter or infusion set to create a fluid path for carrying medication from the reservoir to the body of a user. The electronics system regulates power from the power supply to the motor. The electronics system may include programmable controls to operate the motor continuously or at periodic intervals to obtain a closely controlled and accurate delivery of the medication over an extended period.

The presence of air bubbles in a fluid syringe is undesirable for various reasons. Accordingly, air inside of user-filled syringes is usually expelled before the syringe is used. Moreover, air might be introduced into a pre-filled syringe during the filling and sealing processes. Therefore, various manufacturing techniques are implemented in an attempt to remove air from pre-filled syringes before sealing and/or to minimize the amount of air that gets introduced into the fluid. In this regard, conventional approaches often rely on vacuum filling and/or vacuum stoppering to remove or reduce the amount of air that gets trapped in the pre-filled syringes. Such techniques, however, involve specialized equipment, require additional handling of the product, and result in lower throughput.

Moreover, the piston seal of a pre-filled syringe could be affected by the medication fluid, especially during an extended shelf life. For example, the piston seal might be compressed or flattened against the reservoir wall such that the amount of force required to actuate the piston increases relative to some nominal amount. Increased actuation force may be undesirable, especially in portable devices that rely on battery power. In addition, the sealing characteristics of a piston seal could be degraded by the medication fluid if the pre-filled syringe is not used within an acceptable time period after manufacture.

Accordingly, it is desirable to have a different methodology for handling gas trapped inside of a fluid syringe. In addition, it is desirable to have a syringe piston design and a related syringe piston that can be manipulated to manage the presence of gas inside of the fluid chamber. Furthermore, it is desirable to have improved piston seal configurations that are suitable for use with pre-filled syringes and reservoirs.

BRIEF SUMMARY

An exemplary embodiment of a syringe piston is presented here. The syringe piston includes a piston body and a piston sealing sleeve. The piston body has a fluid end, an actuator end opposite the fluid end, and an outer seal-retaining surface between the fluid end and the actuator end. The piston sealing sleeve is coupled to the piston body around the outer seal-retaining surface. The piston sealing sleeve includes a fin-shaped fluid seal element to form an interference fluid seal with an interior wall of a syringe barrel.

An embodiment of a fluid syringe is also presented here. The fluid syringe includes a syringe barrel having an interior wall and a sealed main fluid chamber, and a syringe piston slidably coupled within the syringe barrel. The syringe piston includes a piston body having a fluid end, an actuator end opposite the fluid end, and an outer seal-retaining surface between the fluid end and the actuator end. The syringe piston also has a piston sealing sleeve coupled to the piston body around the outer seal-retaining surface. The piston sealing sleeve includes a circumferential fluid seal element forming an interference fluid seal against the interior wall, the circumferential fluid seal element having a tapered cross-sectional profile defined by a thick base section and a thin outer section that contacts the interior wall. The syringe piston also includes an end cap coupled to the piston body to retain the piston sealing sleeve on the outer seal-retaining surface.

Also provided is an embodiment of a fluid syringe. The fluid syringe includes a syringe barrel having an interior wall and a sealed main fluid chamber. The fluid syringe also includes a syringe piston slidably coupled within the syringe barrel. The syringe piston includes a piston body having a fluid end, an actuator end opposite the fluid end, an outer seal-retaining surface between the fluid end and the actuator end, and a retaining shoulder integrally formed at the actuator end. The syringe piston also includes a piston sealing sleeve coupled to the piston body around the outer seal-retaining surface, the piston sealing sleeve having a circumferential fluid seal element forming an interference fluid seal against the interior wall, the circumferential fluid seal element having a tapered cross-sectional profile to provide asymmetric deflection characteristics for the circumferential fluid seal element, wherein the retaining shoulder retains the piston sealing sleeve on the piston body.

Another embodiment of a syringe piston is also provided. This embodiment of the syringe piston includes a piston body having a tip, a base opposite the tip, and an outer seal-retaining surface between the tip and the base. The syringe piston also includes a piston sealing cover coupled to the piston body, the piston sealing cover overlying the tip and coupled around the outer seal-retaining surface, and the piston sealing cover having a fin-shaped fluid seal element to form an interference fluid seal with an interior wall of a syringe barrel.

Another embodiment of a fluid syringe is also provided. This embodiment of the fluid syringe includes a syringe barrel having an interior wall and a sealed main fluid chamber, and a syringe piston slidably coupled within the syringe barrel. The syringe piston includes a piston body having a tip, a base opposite the tip, and an outer seal-retaining surface between the tip and the base. The syringe piston also includes a piston sealing cover coupled to the piston body, the piston sealing cover completely covering the tip and overlying at least a portion of the outer seal-retaining surface, the piston sealing cover having a circumferential fluid seal element forming an interference fluid seal against the interior wall, the circumferential fluid seal element having asymmetric deflection characteristics.

A sealing element for a syringe piston is also provided. The sealing element includes a cap portion, a sleeve portion coupled to the cap portion, an interior cavity defined by the cap portion and the sleeve portion, the interior cavity conformally shaped and sized to receive a tip of the syringe piston, and a plurality of circumferential fin-shaped fluid seal elements formed on the sleeve portion. Each of the plurality of circumferential fin-shaped fluid seal elements forms an interference fluid seal with an interior wall of a syringe barrel.

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter.

BRIEF DESCRIPTION OF THE DRAWINGS

A more complete understanding of the subject matter may be derived by referring to the detailed description and claims when considered in conjunction with the following figures, wherein like reference numbers refer to similar elements throughout the figures.

DETAILED DESCRIPTION

Figure 1:
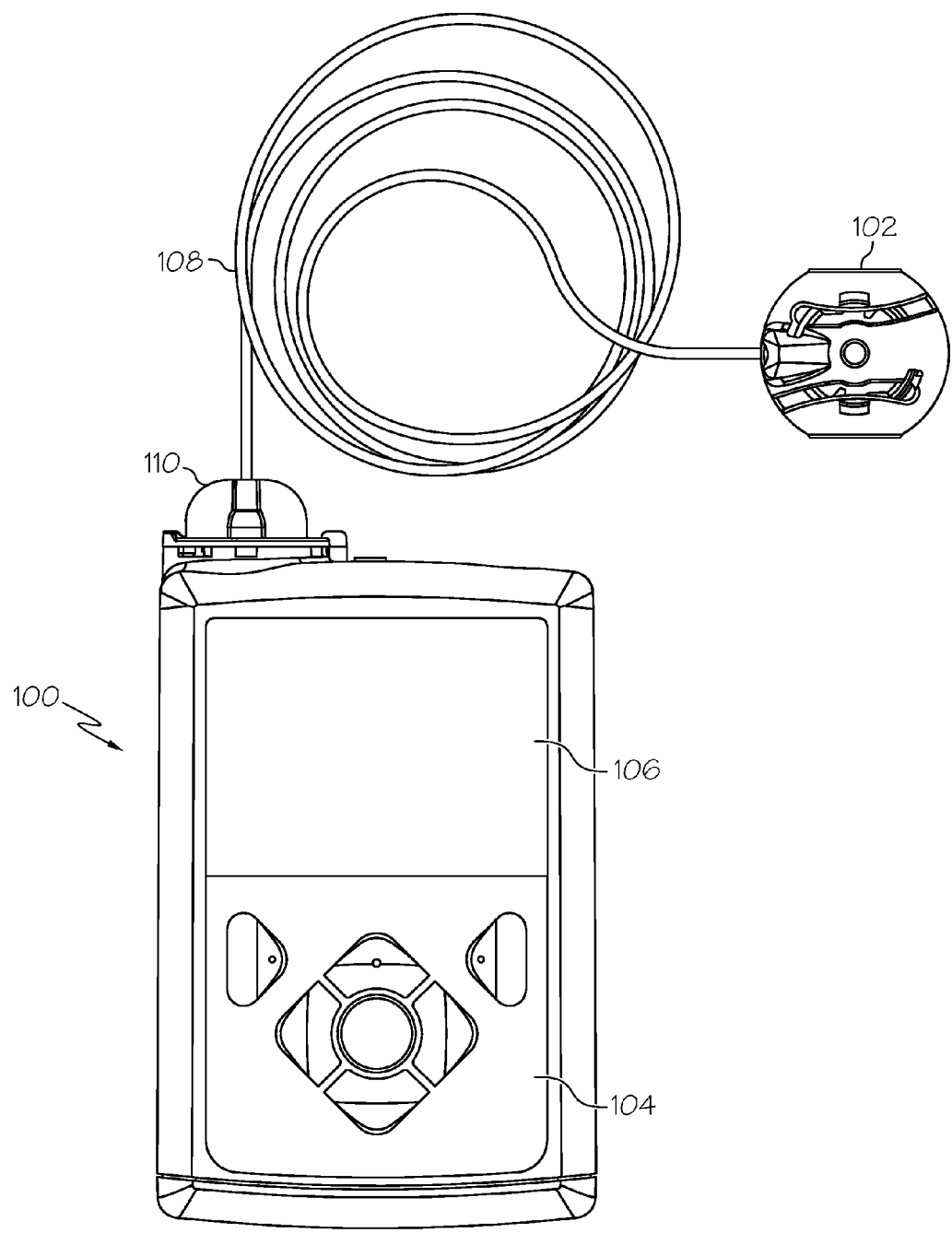
FIG. 1 is a schematic representation of an embodiment of a fluid infusion device.

The following detailed description is merely illustrative in nature and is not intended to limit the embodiments of the subject matter or the application and uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the preceding technical field, background, brief summary or the following detailed description.

Certain terminology may be used in the following description for the purpose of reference only, and thus are not intended to be limiting. For example, terms such as "upper", "lower", "above", and "below" refer to directions in the drawings to which reference is made. Terms such as "front", "back", "rear", "side", "outboard," and "inboard" describe the orientation and/or location of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second" and other such numerical terms referring to structures do not imply a sequence or order unless clearly indicated by the context.

The subject matter presented here relates to a check valve seal for a piston that is used to deliver a fluid (such as a liquid medication) from a fluid syringe to a person. Although the check valve seal concept can be utilized with user-filled syringes or pre-filled syringes, certain benefits described herein apply to pre-filled syringes that do not easily accommodate the expulsion of trapped air by the user. Accordingly, the following description focuses on pre-filled syringe embodiments. Moreover, the following description relates to a fluid infusion device of the type used to treat a medical condition of a patient. The infusion device is used for infusing fluid into the body of a user. The non-limiting examples described below relate to a medical device used to treat diabetes (more specifically, an insulin pump), although embodiments of the disclosed subject matter are not so limited. Accordingly, the infused fluid is insulin in certain embodiments. In alternative embodiments, however, many other fluids may be administered through infusion such as, but not limited to, disease treatments, drugs to treat pulmonary hypertension, iron chelation drugs, pain medications, anti-cancer treatments, medications, vitamins, hormones, or the like. For or the sake of brevity, conventional features and characteristics related to infusion system operation, insulin pump and/or infusion set operation, fluid reservoirs, and fluid syringes may not be described in detail here. Examples of infusion pumps and/or related pump drive systems used to administer insulin and other medications may be of the type described in, but not limited to, United States patent application number 2009/0299290 A1 (the content of which is incorporated by reference in its entirety herein).

The check valve seal and the syringe assembly described here facilitate the containment of entrapped air, which may be introduced or created during the syringe filling process of a pre-filled syringe (after piston seating in the syringe barrel). Some conventional syringe pistons include two seals designed to protect the syringe-filled solutions from environmental conditions. A syringe with the two-seal design might contain solution and air within the syringe after piston installation. Air entrapped in the syringe is only vented by inverting the syringe and expelling a small quantity of solution/air mixture prior to needle injection.

In contrast to conventional syringe designs, the syringe piston described here includes an additional seal (the check valve seal) that faces the fluid chamber. The check valve seal is constructed to serve as a mechanical check valve between the syringe solution and the other piston seals. When positioned upright (i.e., the piston end of the syringe up), the entrapped air in the syringe will rise to the piston base. Thereafter, the piston is engaged (moved toward the solution in the fluid chamber) while the tip of the syringe is sealed. This mode of piston engagement allows entrapped solution/air to pass by the check valve seal into a cavity of the syringe, thereby containing the air and keeping the air out of the syringe solution. The check valve is designed to eliminate backflow of the solution/air mixture from the containment cavity to the syringe solution. Thus, when the syringe is capped or sealed, the check valve seal can be manipulated like a flap to accommodate fluid flow in one direction while inhibiting fluid flow in the other direction.

Figure 2:
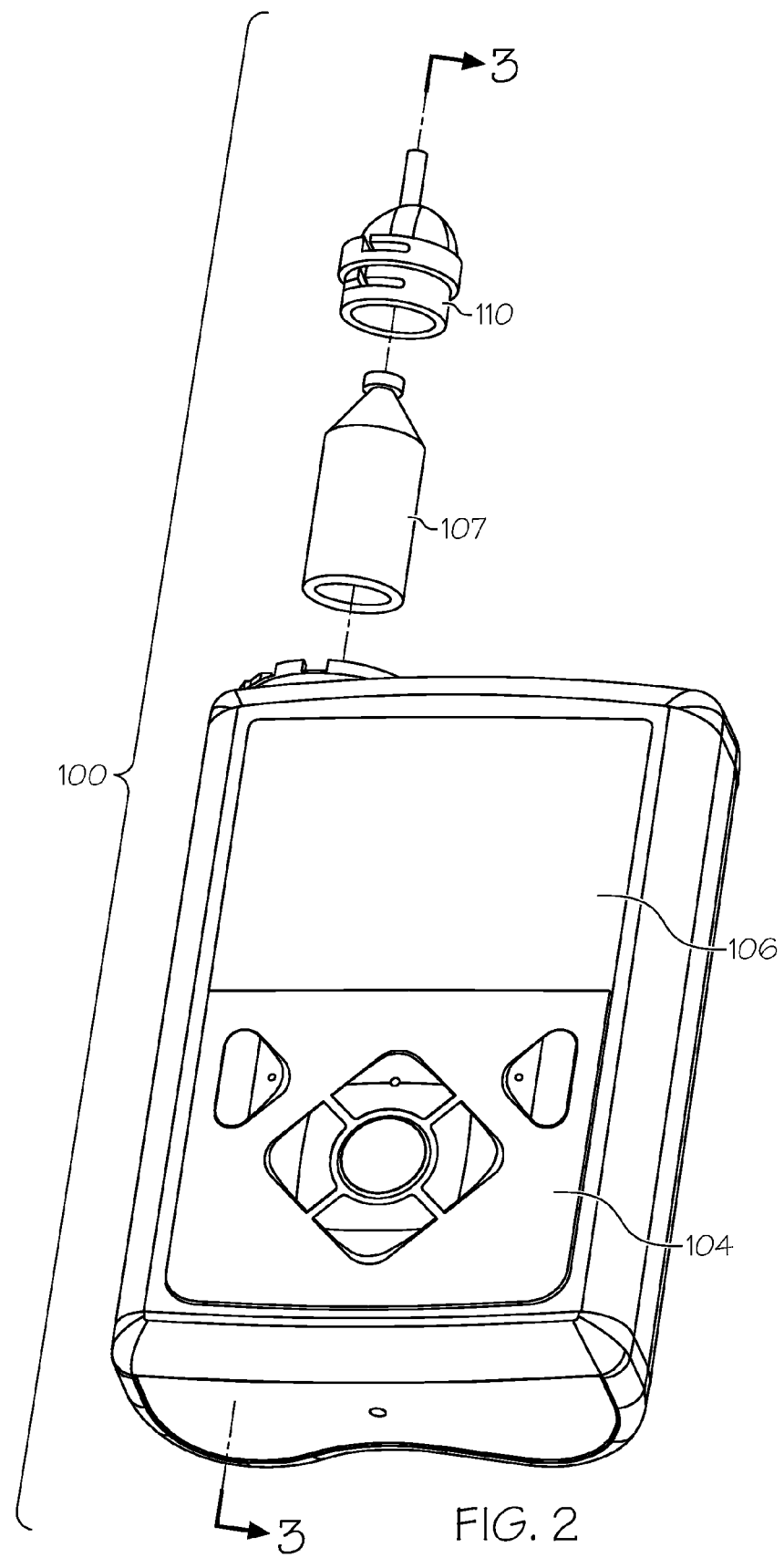
FIG. 2 is an exploded perspective view of the fluid infusion device shown in FIG. 1.

Referring now to the drawings, FIG. 1 is a schematic representation of an embodiment of a fluid infusion device 100, and FIG. 2 is an exploded perspective view of the fluid infusion device 100. FIG. 1 also shows an infusion set 102 coupled to the fluid infusion device 100. The fluid infusion device 100 is designed to be carried or worn by the patient. The fluid infusion device 100 may leverage a number of conventional features, components, elements, and characteristics of conventional and well known fluid infusion devices. For example, the fluid infusion device 100 may incorporate some of the features, components, elements, and/or characteristics described in U.S. Pat. Nos. 6,485,465 and 7,621,893, the relevant content of which is incorporated by reference herein.

Referring to FIG. 1, the fluid infusion device 100 includes a user interface 104 that includes several buttons that can be activated by the user. These buttons can be used to administer a bolus of insulin, to change therapy settings, to change user preferences, to select display features, and the like. Although not required, the illustrated embodiment of the fluid infusion device 100 includes a display element 106. The display element 106 can be used to present various types of information or data to the user, such as, without limitation: the current glucose level of the patient; the time; a graph or chart of the patient's glucose level versus time; device status indicators; etc. In some embodiments, the display element 106 is realized as a touch screen display element and, therefore, the display element 106 also serves as a user interface component.

The fluid infusion device 100 accommodates a fluid syringe 107 (see FIG. 2) for the fluid to be delivered to the user. Note that the words "syringe" and "reservoir" are used interchangeably herein; both refer to a fluid containment component that can be actuated to dispense fluid. A length of tubing 108 fluidly couples the fluid syringe 107 to the infusion set 102. The tubing 108 extends from the fluid infusion device 100 to the infusion set 102, which provides fluid communication with the body of the user. A removable cap or fitting 110 is suitably sized and configured to accommodate replacement of fluid reservoirs (which are typically disposable) as needed. In this regard, the fitting 110 is designed to accommodate the fluid path from the fluid syringe 107 to the tubing 108.

Figure 3:
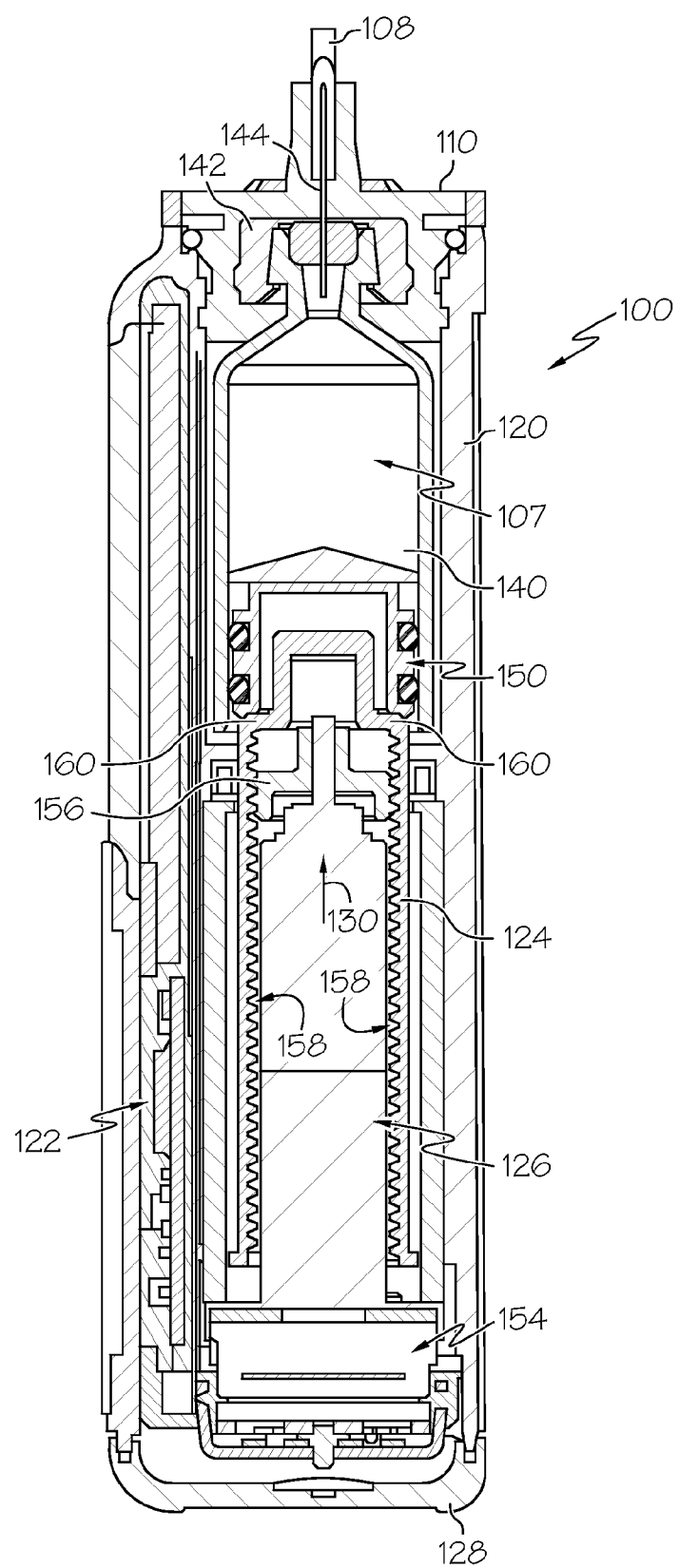
FIG. 3 is a cross-sectional view of the fluid infusion device (as viewed along line 3-3 in FIG. 2) with a fluid syringe installed therein.

FIG. 3 is a cross-sectional view of the fluid infusion device 100 with the fluid syringe 107 installed therein. The illustrated embodiment of the fluid infusion device 100 includes, without limitation: a housing 120; an electronics assembly 122; a slide 124; and a drive system 126. The housing 120 includes an opening adapted to receive the fluid syringe 107. FIG. 3 illustrates the relationship between the drive system 126, the slide 124, and the fluid syringe 107. FIG. 3 shows other components and features that are conventional in nature and/or are unrelated to the subject matter presented here. Moreover, it should be appreciated that FIG. 3 depicts the fluid infusion device 100 in a simplified manner. In practice, the fluid infusion device 100 could include additional elements, features, or components that are not shown or described in detail here.

The housing 120 has a hollow interior that accommodates the electronics assembly 122, the fluid syringe 107, the slide 124, and the drive system 126, which are enclosed within the housing 120 by a bottom portion 128. In the illustrated embodiment, the slide 124, the drive system 126, and the fluid syringe 107 are aligned in an axial direction (indicated by arrow 130). As described in greater detail below, the drive system 126 facilitates displacement of the slide 124 in the axial direction 130 to dispense fluid from the fluid syringe 107.

The electronics assembly 122 includes control electronics that generally represent the hardware, firmware, processing logic and/or software (or combinations thereof) to control operation of the drive system 126 and other features of the fluid infusion device 100. In an exemplary embodiment, the electronics assembly 122 includes one or more programmable controllers that may be programmed to control the various operations of the fluid infusion device 100.

Depending on the embodiment, the fluid syringe 107 may be realized as a disposable reservoir, a user-filled reservoir, a pre-filled reservoir, a vial, a cartridge, or the like. In certain embodiments, the infused fluid is insulin, although many other fluids may be administered through infusion such as, but not limited to, HIV drugs, drugs to treat pulmonary hypertension, iron chelation drugs, pain medications, anti-cancer treatments, medications, vitamins, hormones, or the like. The fluid syringe 107 typically includes a barrel 140 that contains the fluid and is concentrically and/or coaxially aligned with the slide 124 (e.g., in the axial direction 130) when the fluid syringe 107 is installed in the fluid infusion device 100. The fluid delivery end of the fluid syringe 107 may include a suitably configured sealing cap 142 that cooperates with the fitting 110 in a way that allows the fitting 110 to secure the fluid syringe 107 in the housing 120. When the fitting 110 is in place (as depicted in FIG. 3), displacement of the fluid syringe 107 in the axial direction 130 is inhibited. In an exemplary embodiment, the sealing cap 142 includes a penetrable membrane that is punctured by a delivery needle 144 of the fitting 110. In this manner, the fitting 110 secures the fluid syringe 107 within the housing 120 and also serves to secure and connect the fluid syringe 107 to the infusion set tubing 108.

The base end of the fluid syringe 107 (which is near the slide 124) includes a syringe piston 150 positioned to push fluid from inside the barrel 140 of the fluid syringe 107 along a fluid path through the tubing 108 to a user. Note that the words "piston," "stopper," and "plunger" may be used interchangeably herein; these words all refer to the component that moves within the fluid syringe 107 to dispense fluid from the barrel 140. The slide 124 is configured to mechanically couple or otherwise engage with the piston 150, thereby becoming seated with the piston 150. In operation, fluid is forced from the fluid syringe 107 via the tubing 108 as the drive system 126 is actuated to displace the slide 124 in the axial direction 130 toward the sealing cap 142.

In an exemplary embodiment, the drive system 126 includes a motor assembly 154 and a drive screw 156. The motor assembly 154 might include a motor and associated drive train components that convert rotational motor motion to a translational displacement of the slide 124 in the axial direction 130, thereby engaging and displacing the piston 150 of the fluid syringe 107. In some embodiments, the motor assembly 154 may also be powered to rewind the slide 124 in the opposing direction to accommodate removal and replacement of the fluid syringe 107. Although the illustrated embodiment of the fluid infusion device 100 utilizes a coaxially aligned drive system 126, the motor assembly 154 could instead be arranged in an offset or otherwise non-coaxial manner, relative to the longitudinal axis of the fluid syringe 107.

The drive screw 156 mates with internal threads 158 internal to the slide 124. When the motor assembly 154 is powered, the drive screw 156 rotates, and the slide 124 is forced to translate in the axial direction 130. In an exemplary embodiment, the fluid infusion device 100 includes a feature that prevents the slide 124 from rotating when the drive screw 156 rotates. Thus, rotation of the drive screw 156 causes the slide 124 to extend or retract relative to the motor assembly 154. When the fluid infusion device 100 is assembled and operational, the slide 124 contacts the piston 150 to engage the fluid syringe 107 and to control delivery of fluid from the fluid infusion device 100. In an exemplary embodiment, a shoulder portion 160 of the slide 124 contacts or otherwise engages the piston 150 to displace the piston 150 in the axial direction 130. In alternative embodiments (not shown), the slide 124 may include a threaded tip capable of being detachably engaged with internal threads formed in the piston 150, as described in detail in U.S. Pat. Nos. 6,248,093 and 6,485,465, which are incorporated by reference herein.

Figure 4:
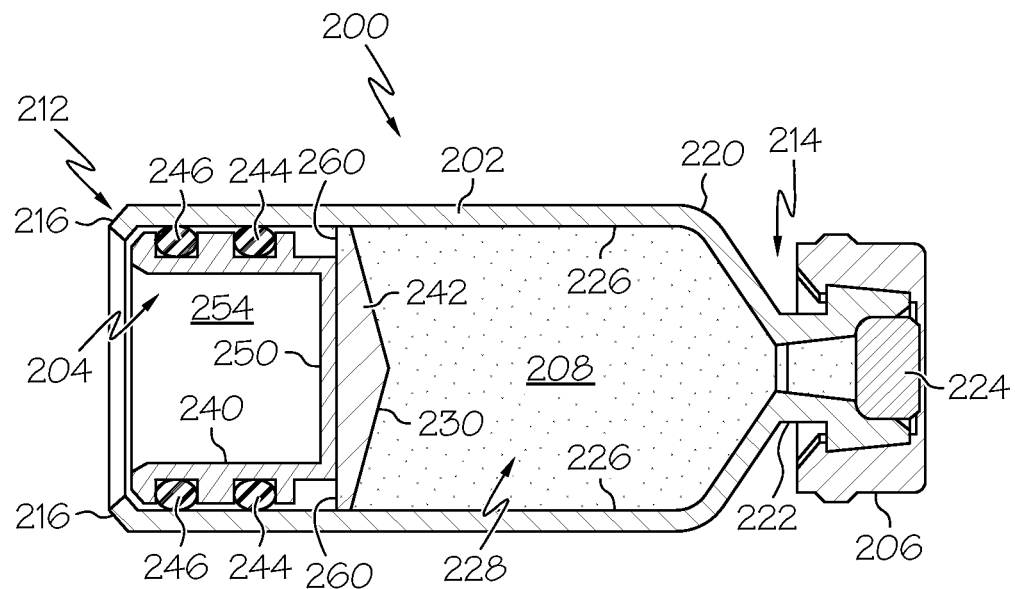
FIG. 4 is a cross-sectional view of an exemplary embodiment of a fluid syringe, taken along its major longitudinal axis.

FIG. 4 is a cross sectional view of an exemplary embodiment of a fluid syringe 200, taken along its major longitudinal axis. Note that the fluid syringe 200 could be used as one suitable embodiment of the fluid syringe 107 shown in FIG. 2 and FIG. 3. This particular embodiment of the fluid syringe 200 is a pre-filled component, and FIG. 4 depicts the fluid syringe 200 in its pre-filled state prior to use and prior to installation into a fluid infusion device. The fluid syringe 200 generally includes, without limitation: a body or barrel 202; a piston 204; a sealing cap 206; and fluid 208 contained in the barrel 202. For this example, the fluid 208 is a liquid medication such as insulin.

The barrel 202 can be formed from plastic, metal, glass, or the like. The barrel 202 has a base end 212 and a cap end 214 opposite the base end 212. The base end 212 may include or cooperate with a retaining feature 216 that is designed to retain the piston 204 within the barrel 202. The retaining feature 216 prevents the piston 204 from slipping out of the barrel 202 during manufacturing, shipping, storage, and handling of the fluid syringe 200. The retaining feature 216 could be realized as an inward protruding rim or shoulder (as depicted in FIG. 4), as one or more keyway features, as a separate ring or other securing component that can be coupled to the fluid syringe 200, or the like. The cap end 214 of the barrel 202 has a generally conical-shaped portion 220 which tapers to a neck region 222. The sealing cap 206 is installed onto the neck region 222, thereby forming a fluid-tight seal. In accordance with conventional reservoir designs, the sealing cap 206 includes a penetrable membrane 224 or an insert that can be pierced by a dispensing needle (as described above with reference to FIG. 3). The penetrable membrane 224 may also be referred to as a "septum." The penetrable membrane 224 is designed to preserve its seal after it is pierced, to minimize leakage of fluid around the dispensing needle.

The barrel 202 has an interior wall 226 that defines a main fluid chamber 228 of the barrel 202. As shown in FIG. 4, the fluid 208 resides within the main fluid chamber 228. The main fluid chamber 228 is sealed after the fluid syringe 200 is filled with the fluid 208; FIG. 4 depicts the main fluid chamber 228 in its sealed state. The end surface 230 of the piston 204 also defines the main fluid chamber 228, which changes volume as the piston 204 is moved within the barrel 202.

The piston 204 is slidably coupled within the barrel 202, such that actuation of the piston 204 results in the delivery of the fluid 208 (when the main fluid chamber 228 is unsealed, for example, by piercing the membrane 224). The piston 204 is suitably designed to form a fluid-tight barrier within the barrel 202 such that the fluid 208 does not leak from the base end 212 of the fluid syringe 200 and such that contaminants do not enter the main fluid chamber 228. This particular embodiment of the piston 204 includes, without limitation: a piston body 240; a check valve seal 242; a piston seal 244; and an end seal 246. The end seal 246 may be realized as a second piston seal, or, in certain embodiments, the piston seal 244 and the end seal 246 may be one and the same. In yet other embodiments, three or more seals could be used with the check valve seal 242.

The piston body 240 can be formed from plastic, metal, glass, or the like. The piston body 240 has a fluid end 250 and an actuator end 252 opposite the fluid end 250. When the piston 204 is installed in the barrel 202, the fluid end 250 is near the main fluid chamber 228. The piston body 240 has a cavity 254 defined therein. The cavity 254 is shaped and sized to receive an actuation component, such as the tip of the slide 124 shown in FIG. 3. The exterior of the piston body 240 includes a number of features that accommodate the check valve seal 242, the piston seal 244, and/or the end seal 246. In this regard, the exterior of the piston body 240 may include one or more of the following features or elements (formed therein, attached thereto, or coupled thereto), without limitation: ridges; shoulders; flanges; protrusions; cavities; rims; slots; holes; seats; grooves; and contours. For the embodiment illustrated in FIG. 4, the piston body 240 includes one circumferential groove that accommodates and retains the end seal 246 and another circumferential groove that accommodates and retains the piston seal 244. The piston body 240 may also include another groove or other feature for the check valve seal 242. The illustrated embodiment, however, includes a check valve seal 242 that is mounted atop the piston body 240 such that the major outer surface of the check valve seal 242 faces the fluid 208. Depending on its design, the check valve seal 242 could be coupled to the piston body 240 by way of a press-fit or snap-fit engagement.

The end seal 246 is coupled to the piston body 240 near the actuator end 252, the check valve seal 242 is coupled to the piston body 240 near the fluid end 250, and the piston seal 244 is coupled to the piston body 240 at a location between the fluid end 250 and the actuator end 252. More specifically, the piston seal 244 is positioned between the check valve seal 242 and the end seal 246, as shown in FIG. 4. The piston seal 244 is formed from a suitable material or composition that enables the piston seal 244 to form an interference fluid seal with the interior wall 226 of the barrel 202. In this regard, the piston seal 244 is preferably formed from a resilient and pliable material such as rubber, plastic, urethane, or the like. In certain embodiments, the piston seal 244 is realized as a rubber o-ring that is coupled around the piston body 240. The end seal 246 may be configured as described above for the piston seal 244 and, indeed, the end seal 246 is identical to the piston seal 244 in some embodiments.

When the piston 204 is installed in the barrel 202, the check valve seal 242 forms an interference fluid seal against the interior wall 226 when the piston 204 is unloaded (i.e., no force is applied to the piston 204). FIG. 4 depicts the check valve seal 242 in this nominal state. In certain embodiments, the check valve seal 242 includes a flap 260 that forms the interference fluid seal with the interior wall 226. As explained below, the flap 260 is intentionally designed with asymmetric deflection characteristics. More specifically, the flap 260 is shaped, sized, and otherwise configured such that it is easier to deflect in the direction toward the actuator end 252, and such that it is difficult to deflect in the direction away from the actuator end 252. In other words, the flap 260 functions as a one-way fluid flow regulator. For this embodiment, the check valve seal 242 is tapered such that it is thinner at its outer perimeter (near the barrel 202). In this regard, the check valve seal 242 may resemble an arrowhead.

In practice, the check valve seal 242 is preferably formed from a resilient and pliable material such as rubber, plastic, urethane, or the like. In certain embodiments, the check valve seal 242 is formed from a material or composition that is different than that used for the piston seal 244 and the end seal 246. In this regard, the piston seal 244 and the end seal 246 may be formed from a resilient material having a first durometer, and the check valve seal 242 may be formed from a different resilient material having a second durometer (e.g., the second durometer is higher than the first durometer). Alternatively, the durometer of the piston seal 244 may be equal to the durometer of the check valve seal 242. Consequently, the static, dynamic, and structural properties of the material used for the check valve seal 242 might be different than the static, dynamic, and structural properties of the material used for the piston seal 244 and the end seal 246.

Figure 5:
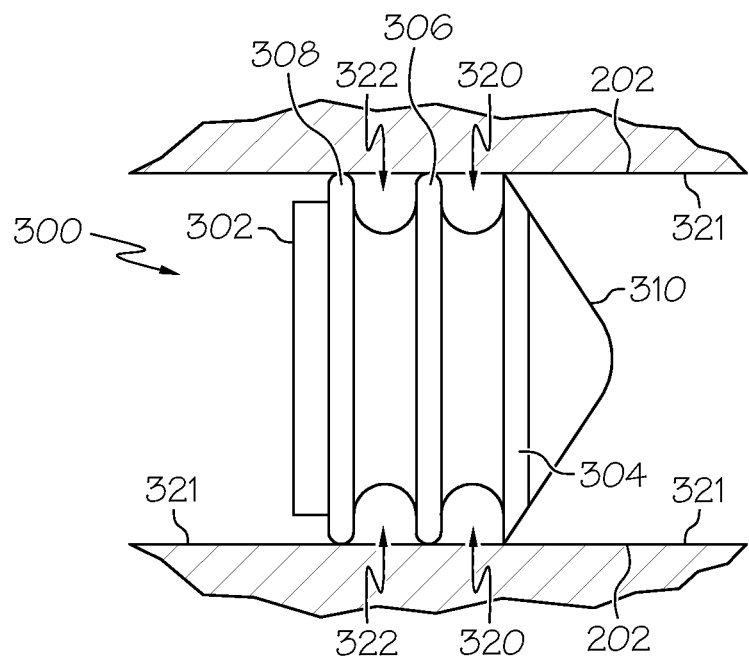
FIG. 5 is a side view of an exemplary embodiment of a syringe piston that is suitable for use with the fluid syringe shown in FIG. 3.

FIG. 5 is a side view of an exemplary embodiment of a syringe piston 300 that is suitable for use with the fluid syringe 200. Many of the features and characteristics of the piston 300 are identical or similar to that described above for the piston 204. Accordingly, common features and aspects of the pistons 204, 300 will not be described in detail here. This embodiment of the piston 300 generally includes, without limitation: a piston body 302; a check valve seal 304; a piston seal 306; and an end seal 308. As described above for the piston 204, the piston seal 306 and the end seal 308 fit within respective grooves formed in the exterior of the piston body 302. Piston 300 also employs a third groove for the check valve seal 304. Thus, the check valve seal 304 may be realized as a ring-shaped seal that is stretched or otherwise manipulated for installation into its retaining groove. In this regard, the fluid end 310 of the piston body 302 is located above the check valve seal 304. This particular embodiment of the check valve seal 304 exhibits a sloped and angled profile, such that its perimeter is very thin at the point of contact with the barrel 202. Notably, the surface of the check valve seal 304 that faces the main fluid chamber slopes downward toward the barrel 202 and toward the end seal 308, as shown in FIG. 5. Of course, the shape, size, and profile of the check valve seal 304 could vary from that shown here.

The pistons 204, 300 are suitably configured with various fluid, gas, and/or buffer zones or chambers defined between the different seals. As best shown in FIG. 5, the piston 300 includes a fluid entrapment zone 320 defined between the check valve seal 304, the piston seal 306, and the interior wall 321 of the barrel 202. In typical implementations, the fluid entrapment zone 320 is utilized as a collection and retention chamber for unwanted air or other gas that might be present after filling the fluid syringe. As described in more detail below, under certain conditions the check valve seal 304 allows one-way fluid flow into the fluid entrapment zone 320 when the syringe piston 300 is installed in the barrel 202. In this regard, when the fluid syringe is deployed and unsealed for purposes of dispensing fluid, the check valve seal 304 forms an interference fluid seal against the interior wall 321 of the barrel 202 and inhibits or prevents fluid flow from the fluid entrapment zone 320 into the main fluid chamber within the barrel 202.

The piston 300 may also include a buffer zone 322 or chamber defined between the piston seal 306, the end seal 308, and the interior wall 321 of the barrel 202. The buffer zone 322 is helpful to inhibit or prevent the incursion of outside contaminants or moisture into the main fluid chamber within the barrel 202. In certain embodiments, the piston seal 306 inhibits or prevents fluid flow from the fluid entrapment zone 320 toward the end seal 308. In other words, the piston seal 306 inhibits or prevents fluid flow from the fluid entrapment zone 320 into the buffer zone 322.

Figure 6:
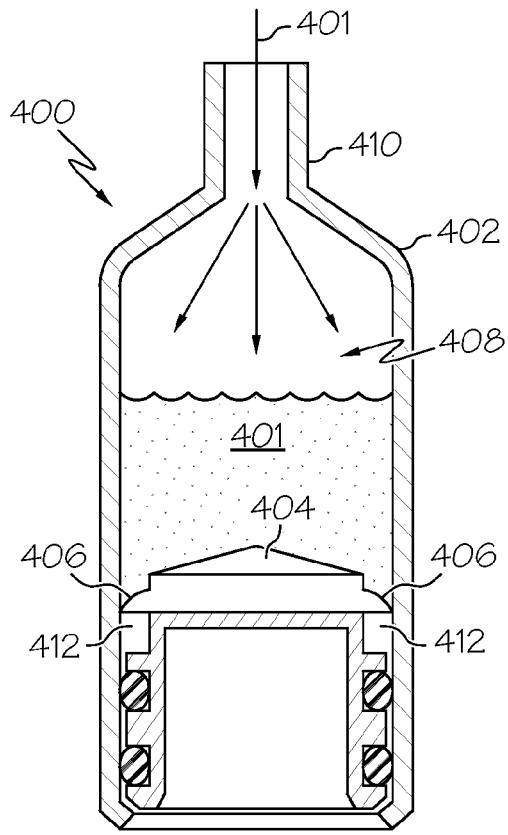
FIGS. 6-10 are diagrams that illustrate a fluid syringe and a method of manufacturing it.

The check valve seals 242, 304 described here facilitate the handling of air or other gas that might become trapped in a pre-filled fluid syringe during manufacturing. In this regard, FIGS. 6-10 are diagrams that illustrate an exemplary embodiment of a fluid syringe and an exemplary method of manufacturing it. FIG. 6 depicts a syringe assembly 400 as it is being filled with a liquid 401. The syringe assembly 400 includes a barrel 402, a piston 404, and a check valve seal 406 having the features and characteristics described above. The piston 404 is depicted in a simplified schematic form in FIGS. 6-10 for the sake of clarity.

Figure 7:
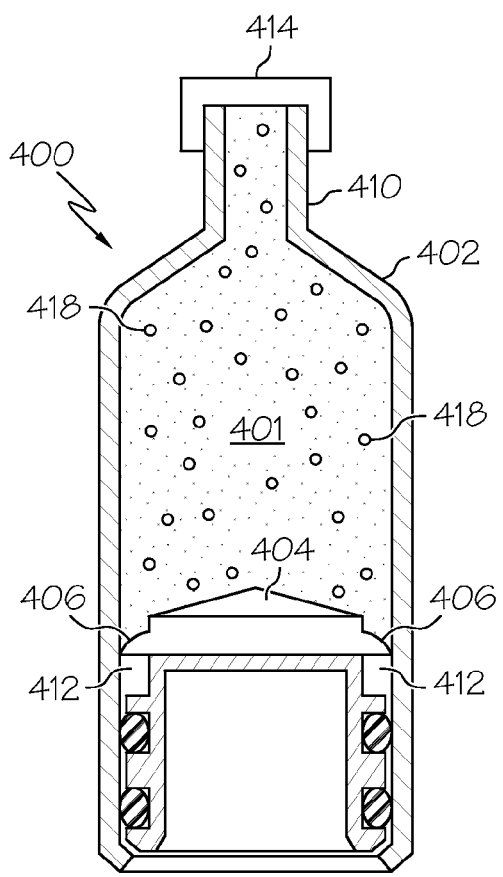

As shown in FIG. 6, the main fluid chamber 408 is filled by dispensing the liquid 401 into the neck region 410 of the barrel 402, which is open or uncapped. In practice, the piston 404 is positioned at or near the bottom of the barrel 402 during the filling operation. This position (shown in FIG. 6) may be considered to be the filling position of the piston 404. The check valve seal 406 cooperates with and seals against the interior wall of the barrel 402 while the liquid 401 is dispensed into the barrel 402. Consequently, the liquid 401 remains above the check valve seal 406 and it does not leak into the fluid containment zone 412. The liquid 401 is dispensed into the neck region 410 until the barrel 402 is filled. Thereafter, the manufacturing process may install a sealing cap 414 onto the neck region 410 to seal the liquid 401 inside the barrel 402 (see FIG. 7). At this time, the barrel 402 and the main fluid chamber are closed (sealed) and the piston 404 is unloaded and in an uncompressed state. Under these conditions the check valve seal 406 maintains the seal against the interior wall of the barrel 402, as shown in FIG. 7.

Figure 8:
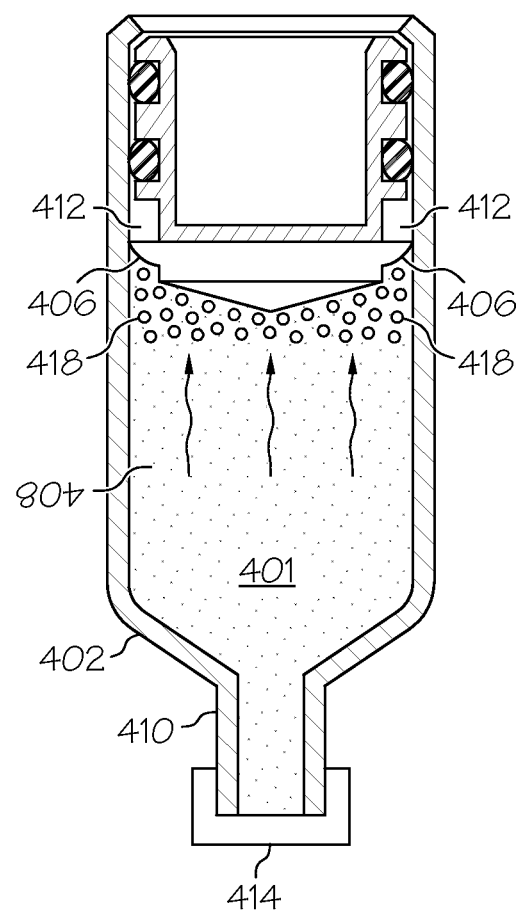

Air or other gas might be introduced into the liquid during the filling process. Moreover, some of this gas can be trapped inside the barrel 402 after securing the sealing cap 414 in place. In this regard, FIG. 7 schematically depicts gas bubbles 418 dispersed throughout the liquid 401 inside the barrel 402. The manufacturing process may continue by inverting the syringe assembly 400 and maintaining it in a position that allows gas in the main fluid chamber to accumulate and rise toward the piston 404 (see FIG. 8). In practice, the syringe assembly 400 should be held in an upright (vertical) position with the check valve seal 406 above the sealing cap 414, to allow the gas bubbles 418 in the liquid 401 to rise, accumulate, and settle at or near the check valve seal 406. The wavy arrows in FIG. 8 represent the rising and settling of the gas near the check valve seal 406. Depending upon the specific manufacturing procedure, the syringe assembly 400 may be held in the settling position without applying any additional stimuli. Alternatively, it may be desirable to accelerate the settling of the gas (if possible) by gently agitating the syringe assembly 400, by changing the surrounding temperature, or the like.

Figure 9A:
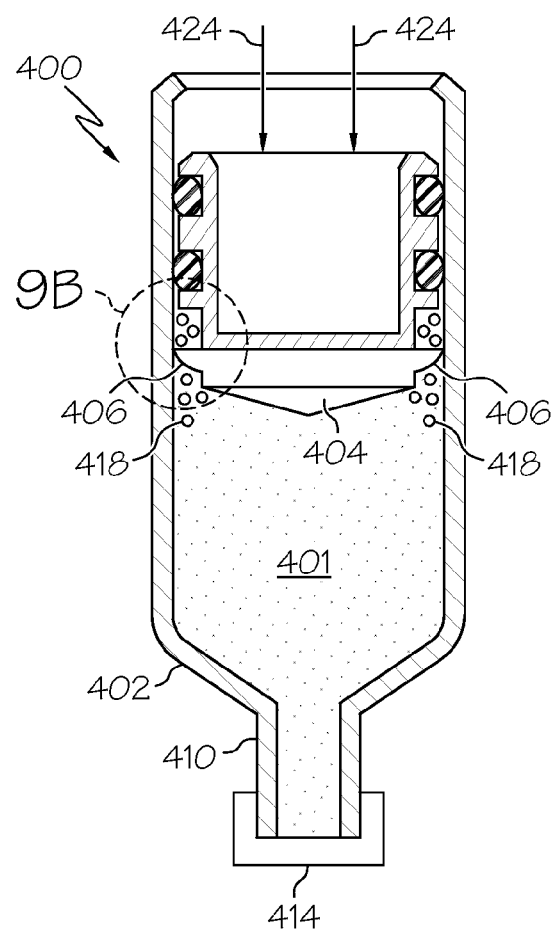
Figure 9B:
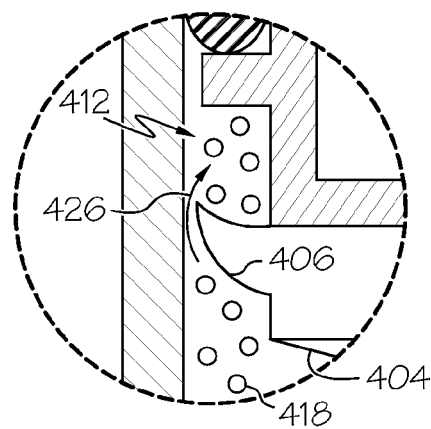

After the gas in the barrel 402 has settled at the check valve seal 406, an actuation force is applied to the piston 404 (while maintaining the syringe assembly 400 in its inverted position). The arrows 424 in FIG. 9 represent the actuation force. The actuation force 424 causes the piston 404 to slightly move into the barrel 402 toward the sealing cap 414, as depicted in FIG. 9. The compression of the piston 404 at this time causes the check valve seal 406 to temporarily disengage from the interior wall of the barrel, as shown in the detail section of FIG. 9. Note that disengagement of the check valve seal 406 in this manner occurs because the barrel 402 and the main fluid chamber are sealed and the piston is loaded under a compressive force. Under these conditions, the check valve seal 406 allows the gas to flow from the main fluid chamber into the fluid entrapment zone 412. The arrow 426 in the detail section of FIG. 9 indicates the flow path of the gas past the check valve seal 406. The piston 404 can be moved into the barrel 402 as far as needed to entrap the desired amount of gas within the fluid entrapment zone 412.

Figure 10:
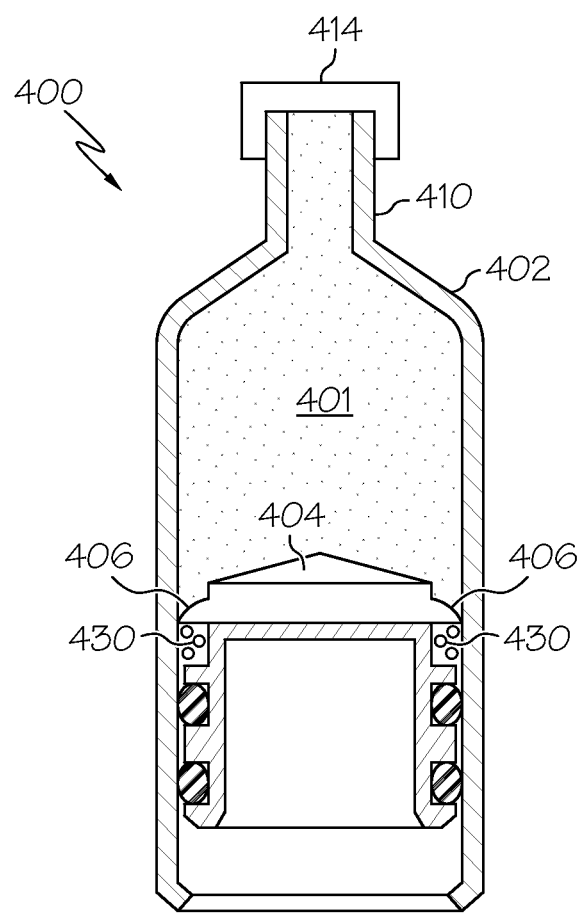

After the desired amount of gas flows past the check valve seal 406 and into the fluid entrapment zone 412, the actuation force 424 is removed from the piston 404 to return the check valve seal 406 to its nominal and unbiased state. FIG. 10 depicts the syringe assembly after removal of the actuation force 424. In this state the check valve seal 406 retains the captured gas 430 in the fluid entrapment zone 412. At this time, manufacturing of the syringe assembly 400 can be completed as desired. The check valve seal 406 is suitably configured to maintain the captured gas 430 in the fluid entrapment zone 412 while fabrication of the syringe assembly 400 is completed, during packaging, shipping, and storage of the syringe assembly 400, and during user manipulation and installation of the syringe assembly 400. In this regard, the captured gas 430 should remain in the fluid entrapment zone 412 after the syringe assembly 400 is installed in a fluid infusion device (see FIG. 3). Moreover, the captured gas 430 remains in the fluid entrapment zone 412 after the syringe assembly 400 has been opened (unsealed) for purposes of dispensing fluid. In particular, the check valve seal 406 maintains its seal against the interior wall of the barrel 402 when the main fluid chamber is unsealed (e.g., the sealing cap 414 has been penetrated), and when the piston is compressed for purposes of delivering the liquid out of the barrel 402.

Accordingly, the check valve seals described above can be utilized with a piston of a fluid reservoir such that the reservoir can be pre-filled in an easy and cost efficient manner without performing time consuming and complicated procedures intended to completely eliminate the presence of gas or air during filling. Rather, the check valve seals allow a manufacturer of pre-filled reservoirs to tolerate and accommodate some amount of gas that might be trapped inside the sealed reservoirs. The check valve seals, along with the manufacturing procedure described above, can be used to collect and capture the trapped gas without having to perform a post-fill venting or priming operation.

Alternative Seal Configurations

The syringe piston embodiments described above utilize a check valve seal for purposes of gas entrapment. Alternate configurations, however, need not always utilize a check valve seal. The following section presents several alternative embodiments of a syringe piston that employs fin-shaped or tapered sealing features for establishing the fluid seal between the syringe piston and the inner wall of the syringe barrel. Although the various embodiments described below are particularly suitable for use with pre-filled syringes, they could also be used with refillable or patient-filled disposable syringes.

Pre-filled syringes that contain medication fluid must satisfy certain shelf life requirements such that the medication fluid and the syringes themselves maintain their integrity and usefulness from the time of manufacture to the time of use. In certain situations, however, long shelf life may affect the static and/or dynamic properties of the syringe piston. For example, if traditional o-ring seals are utilized for the fluid seal between the piston and the syringe barrel, then the o-ring seals may become compressed or otherwise lose their original shape over time. As a result, the amount of force required to initiate movement of the piston and/or the amount of gliding force needed to keep the piston moving during delivery of the fluid may increase with long shelf life. Ideally, the breaking and gliding forces should remain nearly constant and predictable regardless of the age of the syringe, such that the infusion pump motor and battery are not overtaxed.

The exemplary embodiments described below utilize one or more circumferential fin-shaped sealing elements to create the fluid seal between the piston syringe and the reservoir barrel. The shape and configuration of the sealing element(s) reduce the compression load needed to glide the syringe piston in the forward direction. The fin-shaped sealing elements are less susceptible to the adverse effects of long shelf life and, therefore, maintain their static and dynamic friction characteristics, resulting in consistent and predictable actuation once deployed.

Figure 11:
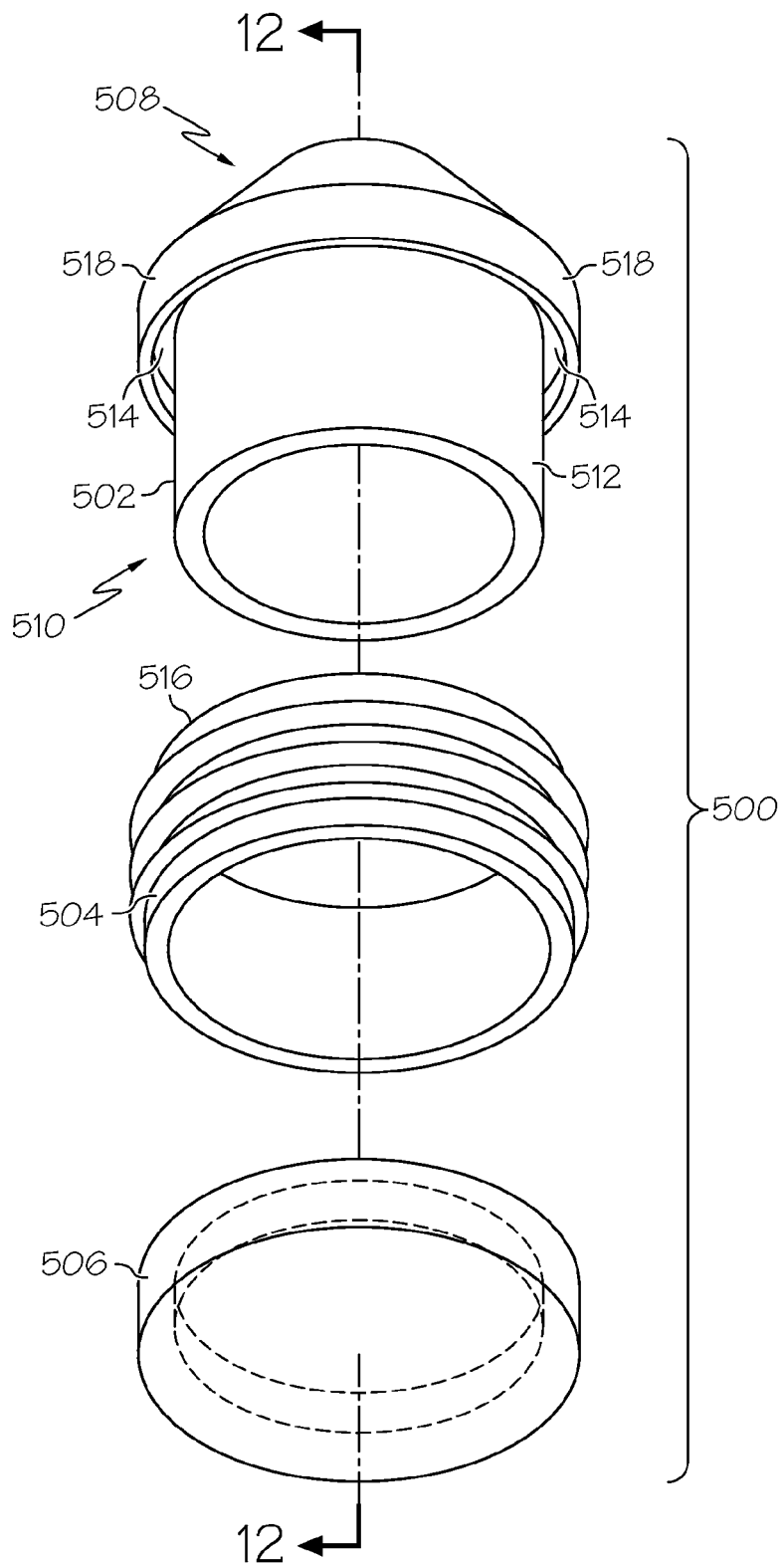
FIG. 11 is an exploded perspective view of an exemplary embodiment of a syringe piston that employs a piston sealing sleeve.
Figure 12:
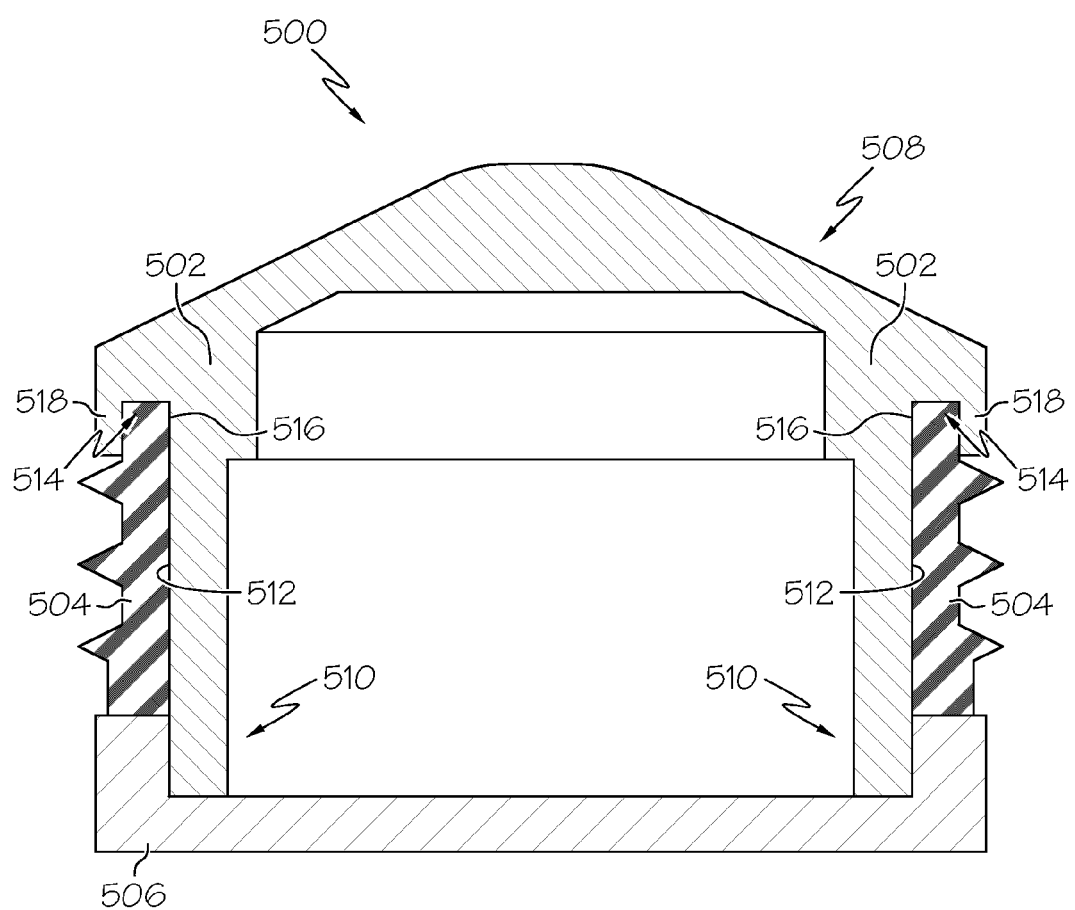
FIG. 12 is a cross-sectional view of the syringe piston as assembled and viewed along line 12-12 in FIG. 11.

FIGS. 11-15 depict one exemplary embodiment of a syringe piston 500 that includes three primary components. FIG. 11 is an exploded perspective view of the piston 500, FIG. 12 is a cross-sectional view of the piston 500 as assembled and viewed along line 12-12 in FIG. 11, and FIGS. 13-15 are cross-sectional detail views of various sealing features of the piston 500. It should be appreciated that an embodiment of the piston 500 might share some of the features, elements, and functionality described above for the syringe pistons that utilize check valves. For the sake of brevity and clarity, common features and functionality will not be redundantly described in detail in the context of the piston 500 or in the context of any of the alternative embodiments presented below.

The illustrated embodiment of the piston 500 includes, without limitation: a piston body 502; a piston sealing sleeve 504; and an end cap 506. These three primary components are assembled and coupled together in an appropriate manner, resulting in the assembly depicted in FIG. 12. The piston 500 can be provided with a fluid syringe for maintaining an interference fluid seal against the interior wall of the syringe barrel, as described above (see, for example, FIGS. 3-5 and the related description).

The piston body 502 has a fluid end 508 and an actuator end 510 opposite the fluid end 508. The fluid end 508 corresponds to the tip of the piston body 502, and the actuator end 510 corresponds to the base or bottom of the piston body 502. The piston body 502 has an outer seal-retaining surface 512 that is located between the fluid end 508 and the actuator end 510. For this particular embodiment, the outer seal-retaining surface 512 represents a straight outer surface of a cylinder, as best shown in FIG. 11. The outer seal-retaining surface 512 extends from the fluid end 508 and it may continue until the bottom of the piston body 502. The outer seal-retaining surface 512 may be relatively smooth (as depicted), or it may be textured to provide a grip for the piston sealing sleeve 504 and/or to accommodate the use of an adhesive to join the piston sealing sleeve 504 to the piston body 502.

The piston body 502 may include a retaining lip 514 that is shaped and sized in accordance with a rim 516 of the piston sealing sleeve 504. When the piston 500 is assembled (see FIG. 12), the retaining lip 514 receives the rim 516 and maintains the piston sealing sleeve 504 in position around the outer seal-retaining surface 512. As shown in FIG. 11, the retaining lip 514 is realized as a circumferential groove or channel that is located under the fluid end 508 of the piston body 502. Thus, the rim 516 of the piston sealing sleeve 504 resides between the outer seal-retaining surface 512 and an outer wall 518 that extends from the fluid end 508 toward the actuator end 510.

The piston sealing sleeve 504 is shaped and sized to mate with the piston body 502. As shown in FIG. 12, the piston sealing sleeve 504 is coupled to the piston body 502 around the outer seal-retaining surface 512, and the piston sealing sleeve 504 is held in place with the retaining lip 514 at one end and with the end cap 506 at the other end. In practice, the piston sealing sleeve 504 is shaped and sized for installation onto the piston body 502, perhaps with some amount of compression on the outer seal-retaining surface 512. The piston sealing sleeve 504 is preferably formed from a resilient and pliable material such as rubber, plastic, urethane, silicone, bromobutyl rubber, chlorobutyl rubber, or the like. In certain embodiments, the piston sealing sleeve 504 may include or be treated with a lubricant coating such as silicone fluid, a silicone copolymer, a fluoropolymer, PARYLENE polymer, or the like. The particular composition of the piston sealing sleeve 504 can be chosen to provide the desired static, dynamic, and mechanical characteristics and properties as required by the given application. In certain embodiments, the piston sealing sleeve 504 is manufactured as an integral one-piece component.

The end cap 506 is coupled to the piston body 502 and/or to the piston sealing sleeve 504. In preferred implementations, the end cap 506 is affixed to the piston body 502 and/or to the piston sealing sleeve 504 to retain the piston sealing sleeve 504 on the outer seal-retaining surface 512. As shown in FIG. 11, the end cap 506 may be generally ring-shaped to accommodate a slide 124 (see FIG. 3) or other actuation mechanism. The manner in which the end cap 506 is implemented and attached to the piston 500 may vary from one embodiment to another.

Figure 13:
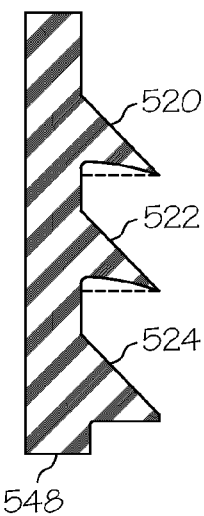
FIGS. 13-15 are cross-sectional detail views of various sealing features of the piston sealing sleeve shown in FIG. 11.
Figure 14:
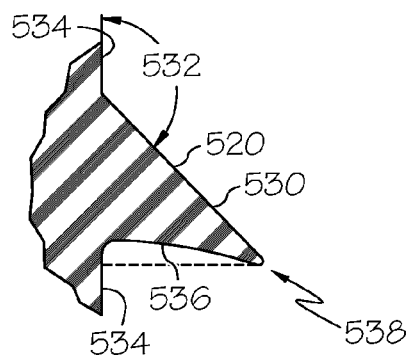
Figure 15:
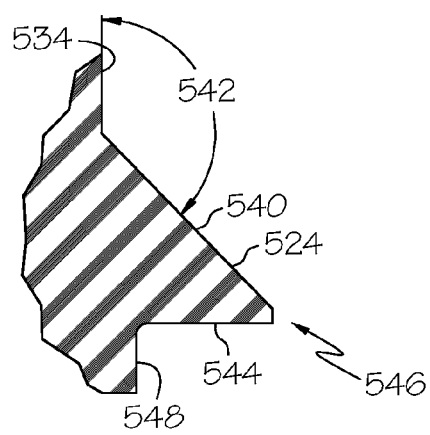

Referring to FIGS. 13-15, the illustrated embodiment of the piston sealing sleeve 504 includes three fin-shaped sealing elements configured to form an interference fluid seal with the interior wall of the syringe barrel (in alternative embodiments, more or less than three sealing elements could be utilized). More specifically, the piston sealing sleeve 504 includes an upper fin-shaped fluid seal element 520, a lower fin-shaped fluid seal element 522, and a fin-shaped end seal element 524. The lower fin-shaped fluid seal element 522 is located between the upper fin-shaped fluid seal element 520 and the fin-shaped end seal element 524. The fin-shaped end seal element 524 is located between the lower fin-shaped fluid seal element 522 and the actuator end 510 of the piston body 502. FIG. 13 depicts these seal elements in cross-section; it should be appreciated that the seal elements continue around the entire circumference of the piston sealing sleeve 504, effectively forming three finned rings around the piston sealing sleeve 504. Although not always required, for the illustrated embodiment the seal elements 520, 522, 524 are integrally formed with the piston sealing sleeve 504.

Referring to FIG. 13, each of the fin-shaped seal elements 520, 522, 524 has a tapered cross-sectional profile such that it exhibits asymmetric deflection characteristics. More specifically, each of the fin-shaped seal elements 520, 522, 524 is shaped, sized, and otherwise configured such that it is easier to deflect in the direction toward the actuator end 510, and such that it resists deflection in the direction toward the fluid end 508. In other words, fin-shaped seal elements 520, 522, 524 provide a good fluid seal against the barrel of the syringe while accommodating movement and gliding of the piston 500 in the direction normally associated with fluid delivery (see FIG. 3).

For this particular embodiment, each fin-shaped seal element 520, 522, 524 is defined by a relatively thick base section (i.e., the portion that originates at the primary "wall" section of the piston sealing sleeve 504) and a relatively thin or narrowed outer section (i.e., the portion extending from the base section, which terminates at the outermost section that contacts the interior wall of the syringe barrel). As shown in FIGS. 13-15, each seal element 520, 522, 524 exhibits a generally triangular cross-sectional profile such that each seal element 520, 522, 524 becomes thinner as a function of its distance away from the piston body 502. Thus, each seal element 520, 522, 524 terminates at a very thin edge that resembles a point when viewed in cross-section.

FIG. 14 is a cross-sectional detail view of the fin-shaped seal element 520 in its natural uncompressed and non-deflected state (the natural profile of the fin-shaped seal element 522 is identical to that shown in FIG. 14). For this exemplary embodiment, the upper surface 530 of the seal element 520—the surface that faces the fluid end 508 of the piston body 502—is nominally flat, and it forms an angle 532 with the outer wall 534 of the piston sealing sleeve 504. In certain embodiments, the angle 532 is about 135 degrees, although different angles may be suitable in other embodiments. The lower surface 536 of the seal element 520—the surface that faces the actuator end 510 of the piston body 502—is concave. In other words, the lower surface 536 is dished inwardly, as shown in FIG. 14. Moreover, the terminating tip 538 of the seal element 520 is fabricated with a radius to facilitate movement and gliding of the piston 500.

FIG. 15 is a cross-sectional detail view of the fin-shaped end seal element 524 in its natural uncompressed and non-deflected state. As described above for the seal element 520, the upper surface 540 of the seal element 524 is nominally flat, and the upper surface 540 forms an angle 542 of approximately 135 degrees with the outer wall 534 of the piston sealing sleeve 504. In contrast to the lower surface 536 of the fin-shaped seal element 520, the lower surface 544 of the end seal element 524 is flat. This configuration is desirable to reduce the contact surface with the inner surface of the barrel, thereby reducing dynamic friction and stiction forces. Moreover, the terminating tip 546 of the end seal element 524 is fabricated with a flat segment that contacts the syringe barrel. This configuration is desirable to maintain the concentricity of the plunger during insertion and movement. In further contrast to the fin-shaped seal element 520, the end seal element 524 is supported by a thicker base section 548 (also shown in FIG. 13). As depicted in FIG. 13, the base section 548 extends outward and corresponds to a larger wall thickness relative to the wall thickness measured at the equivalent location for the fin-shaped seal elements 520, 522. This added thickness is desirable to increase rigidity while maintaining the sealing capability.

Figure 16:
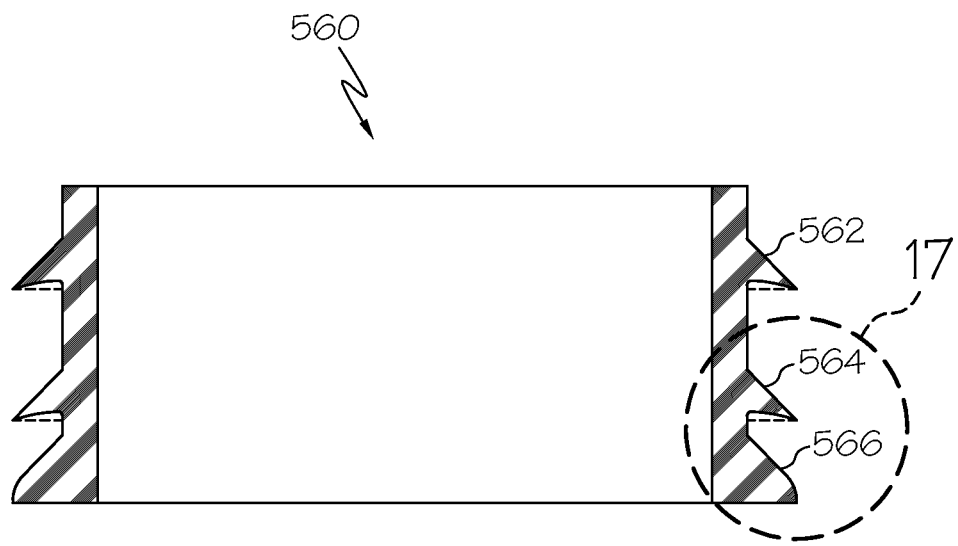
FIG. 16 is a cross-sectional view of another exemplary embodiment of a piston sealing sleeve.

FIG. 16 is a cross-sectional view of another exemplary embodiment of a piston sealing sleeve 560, which could be used in lieu of the piston sealing sleeve 504 described above. The piston sealing sleeve 560 includes an upper fin-shaped fluid seal element 562 and a lower fin-shaped fluid seal element 564, which are similar in shape and configuration to the seal elements 520, 522 described above (in practice, the piston sealing sleeve 560 could include only one fin-shaped seal element or more than two if so desired). The piston sealing sleeve 560 also includes an end seal element 566. In contrast to the arrangement utilized by the piston sealing sleeve 504, the lower fin-shaped fluid seal element 564 is biased toward the end seal element 566. This biasing is desirable to increase rigidity and stability during assembly of the piston. Moreover, the shape and profile of the end seal element 566 is unlike that employed for the fin-shaped end seal element 524. Indeed, the end seal element 566 exhibits a rounded and bulbous profile rather than a fin-shaped profile. This rounded profile may be desirable for ease of manufacturing and processing.

Figure 17:
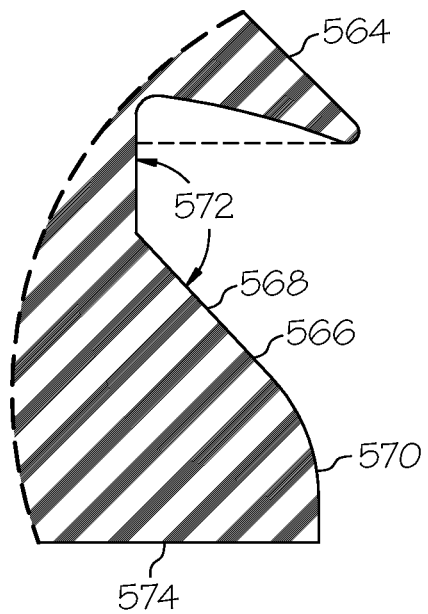
FIG. 17 is a cross-sectional detail view of various sealing features of the piston sealing sleeve shown in FIG. 16.

FIG. 17 is a cross-sectional detail view of the sealing features of the piston sealing sleeve 560. In particular, FIG. 17 shows the end seal element 566 in more detail. Notably, the end seal element 566 includes a generally flat and straight upper surface 568 that transitions to a curved sealing surface 570. As described above for the piston sealing sleeve 504, the upper surface 568 forms an angle 572 with the outer wall of the piston sealing sleeve 560. In certain embodiments, the angle 572 is about 135 degrees, although different angles may be suitable in other embodiments. The lower surface 574 of the end seal element 566 is flat and straight in this particular embodiment.

Figure 18:
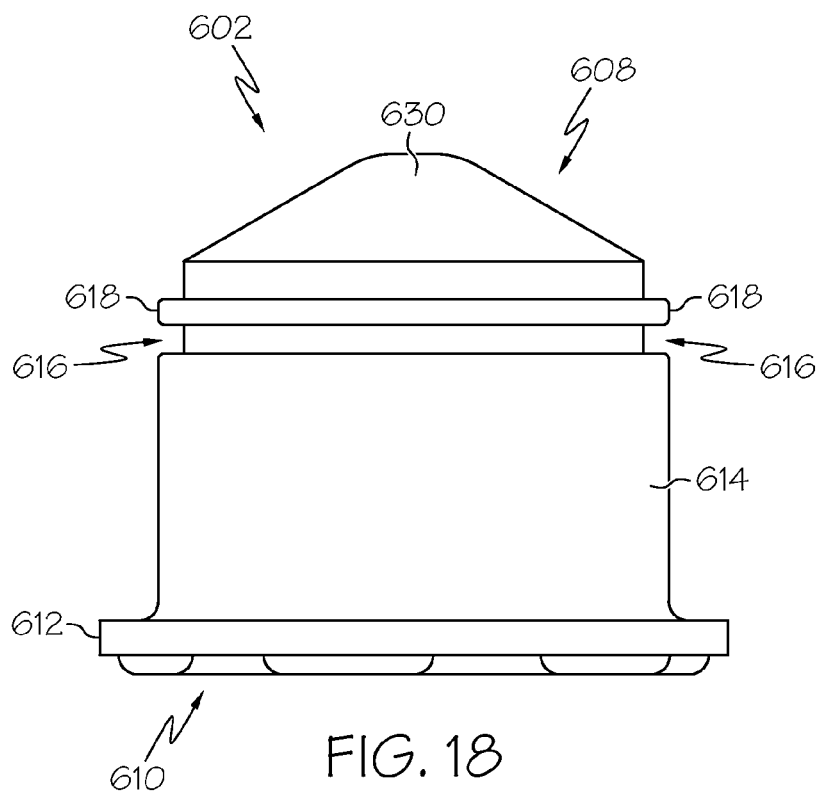
FIG. 18 is a side view of another exemplary embodiment of a piston body suitable for use with a syringe piston.
Figure 19:
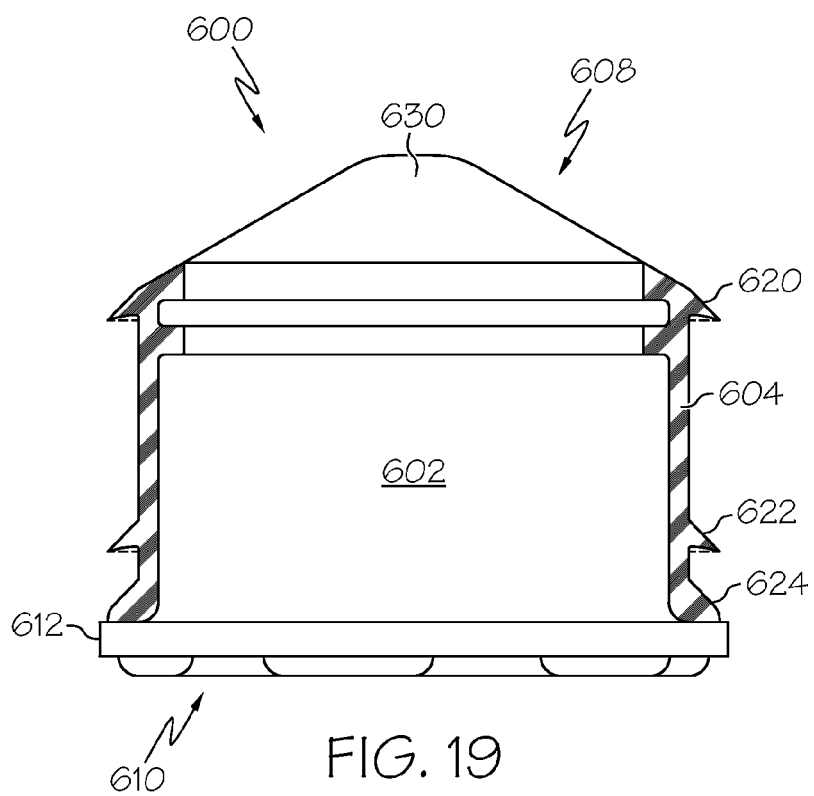
FIG. 19 is a cross-sectional view of a syringe piston that employs the piston body shown in FIG. 18.
Figure 20:
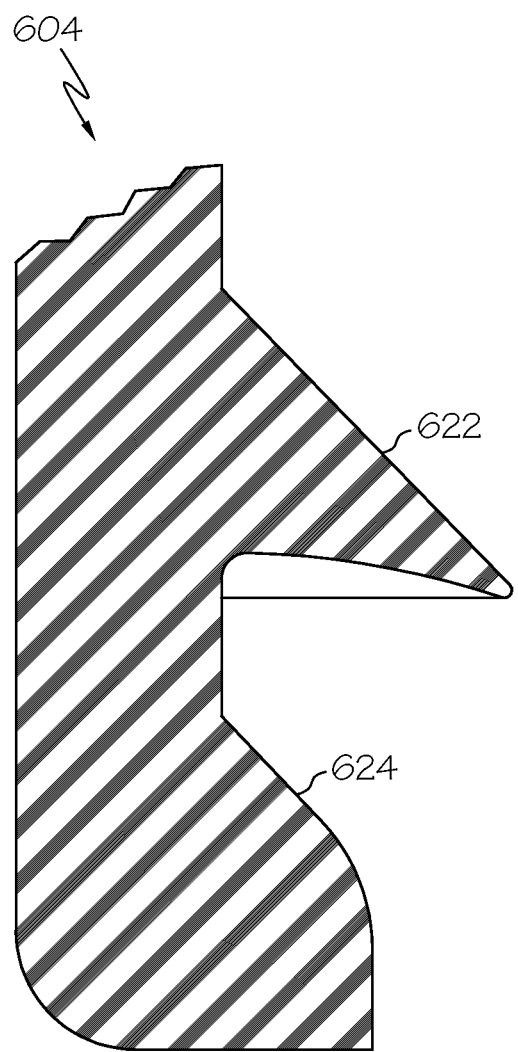
FIG. 20 is a cross sectional detail view of various sealing features of the piston sealing sleeve shown in FIG. 19.

FIGS. 18-20 depict another exemplary embodiment of a syringe piston 600 that includes two primary components. FIG. 18 is a side view of a piston body 602 suitable for use with the syringe piston 600, FIG. 19 is a cross-sectional view of the syringe piston 600, and FIG. 20 is a cross sectional detail view of various sealing features of the syringe piston 600. It should be appreciated that an embodiment of the piston 600 might share some of the features, elements, and functionality described above for the syringe pistons that utilize check valves and/or that described above for the syringe piston 500. For the sake of brevity and clarity, common features and functionality will not be redundantly described in detail in the context of the piston 600 or in the context of any of the alternative embodiments presented below.

The illustrated embodiment of the piston 600 includes, without limitation: a piston body 602 and a piston sealing sleeve 604. These two primary components are assembled and coupled together in an appropriate manner, resulting in the assembly depicted in FIG. 19. In practice, the piston sealing sleeve 604 could be affixed to the piston body 602 using an adhesive, by bonding or welding, and/or by a compression fit. As described in more detail below, the piston sealing sleeve 604 and the piston body 602 include certain features that cooperate to keep the piston sealing sleeve 604 in place on the piston body 602. Notably, the two-piece construction may be desirable to reduce cost, simplify assembly, and improve manufacturability.

Referring to FIG. 18, the piston body 602 has a fluid end 608 and an actuator end 610 opposite the fluid end 608. This particular embodiment of the piston body 602 employs a retaining shoulder 612 (or lip) integrally formed at the actuator end 610. The retaining shoulder 612 extends in the outward radial direction and it is configured to retain the piston sealing sleeve 604 on the piston body 602, as shown in FIG. 19. In this regard, the end of the piston sealing sleeve 604 abuts the retaining shoulder 612 such that the piston sealing sleeve 604 does not slide off of the end of the piston body 602 under normal operating conditions. Accordingly, the syringe piston 600 need not include a separate end cap (see FIG. 11 and FIG. 12).

The piston body 602 has an outer seal-retaining surface 614 that is located between the fluid end 608 and the actuator end 610. For this particular embodiment, the outer seal-retaining surface 614 represents a straight outer surface of a cylinder, as best shown in FIG. 18. The outer seal-retaining surface 614 extends from the fluid end 608 and it may continue until the retaining shoulder 612. The outer seal-retaining surface 614 may be relatively smooth (as depicted), or it may be textured to provide a grip for the piston sealing sleeve 604 and/or to accommodate the use of an adhesive to join the piston sealing sleeve 604 to the piston body 602.

The illustrated embodiment utilizes cooperating features to help keep the piston sealing sleeve 604 positioned correctly on the piston body 602. For example, the piston body 602 may include at least one external circumferential groove 616 formed therein and/or at least one external circumferential tongue 618 formed thereon. These features may be integrally formed in the piston body 602, which in various embodiments is manufactured as a one-piece molded plastic component. Although the groove 616 and the tongue 618 can be located anywhere on the piston body 602, the exemplary implementation depicted in FIG. 18 and FIG. 19 is configured such that the groove 616 and the tongue 618 are both located at or near the fluid end 608 of the piston body 602. As shown in FIG. 19, the piston sealing sleeve 604 includes corresponding features that mate with the groove 616 and the tongue 618 when the syringe piston 600 is assembled. More specifically, the piston sealing sleeve 604 includes at least one internal circumferential tongue formed thereon and configured to mate with the at least one external circumferential groove 616 to retain the piston sealing sleeve 604 on the piston body 602. Similarly, the piston sealing sleeve 604 may include at least one internal circumferential groove formed therein and configured to mate with the at least one external circumferential tongue 618 to retain the piston sealing sleeve 604 on the piston body 602.

The piston sealing sleeve 604 is shaped and sized to mate with the piston body 602 and to cooperate with the groove 616 and tongue 618 as mentioned above. As shown in FIG. 19, the piston sealing sleeve 604 is coupled to the piston body 602 around the outer seal-retaining surface 614, and the piston sealing sleeve 604 is held in place with the retaining shoulder 612 at one end and with the groove 616 and tongue 618 the other end. In practice, the piston sealing sleeve 604 can be installed onto the piston body 602 by stretching it in the radial direction, slipping it over the fluid end 608 of the piston body 602, and manipulating it such that it seats properly on the piston body 602 and such that it mates with the groove 616 and the tongue 618.

Referring to FIG. 19, the illustrated embodiment of the piston sealing sleeve 604 includes three sealing elements configured to form an interference fluid seal with the interior wall of the syringe barrel (alternatively, more or less than three distinct sealing elements could be used). More specifically, the piston sealing sleeve 604 includes an upper fin-shaped fluid seal element 620, a lower fin-shaped fluid seal element 622, and an end seal element 624. The lower fin-shaped fluid seal element 622 is located between the upper fin-shaped fluid seal element 620 and the end seal element 624. The end seal element 624 is located between the lower fin-shaped fluid seal element 622 and the actuator end 610 of the piston body 602.

The general characteristics of the lower fin-shaped fluid seal element 622 and the end seal element 624 are similar to the corresponding characteristics described above for the seal elements 520, 566. The upper fin-shaped fluid seal element 620 also has a tapered cross-sectional profile such that it exhibits asymmetric deflection characteristics (as described above). The seal element 620 is positioned at the fluid end 608 such that it forms a smooth transition to the conical tip 630 of the piston body 602. FIG. 19 shows how the seal element 620 is angled toward the conical tip 630 and how the upper surface of the seal element 620 is substantially continuous with the exposed surface of the conical tip 630. The fin-shaped and tapered portion of the seal element 622, however, is arranged and configured in a manner similar to that described above for the fin-shaped fluid seal element 520.

Figure 21:
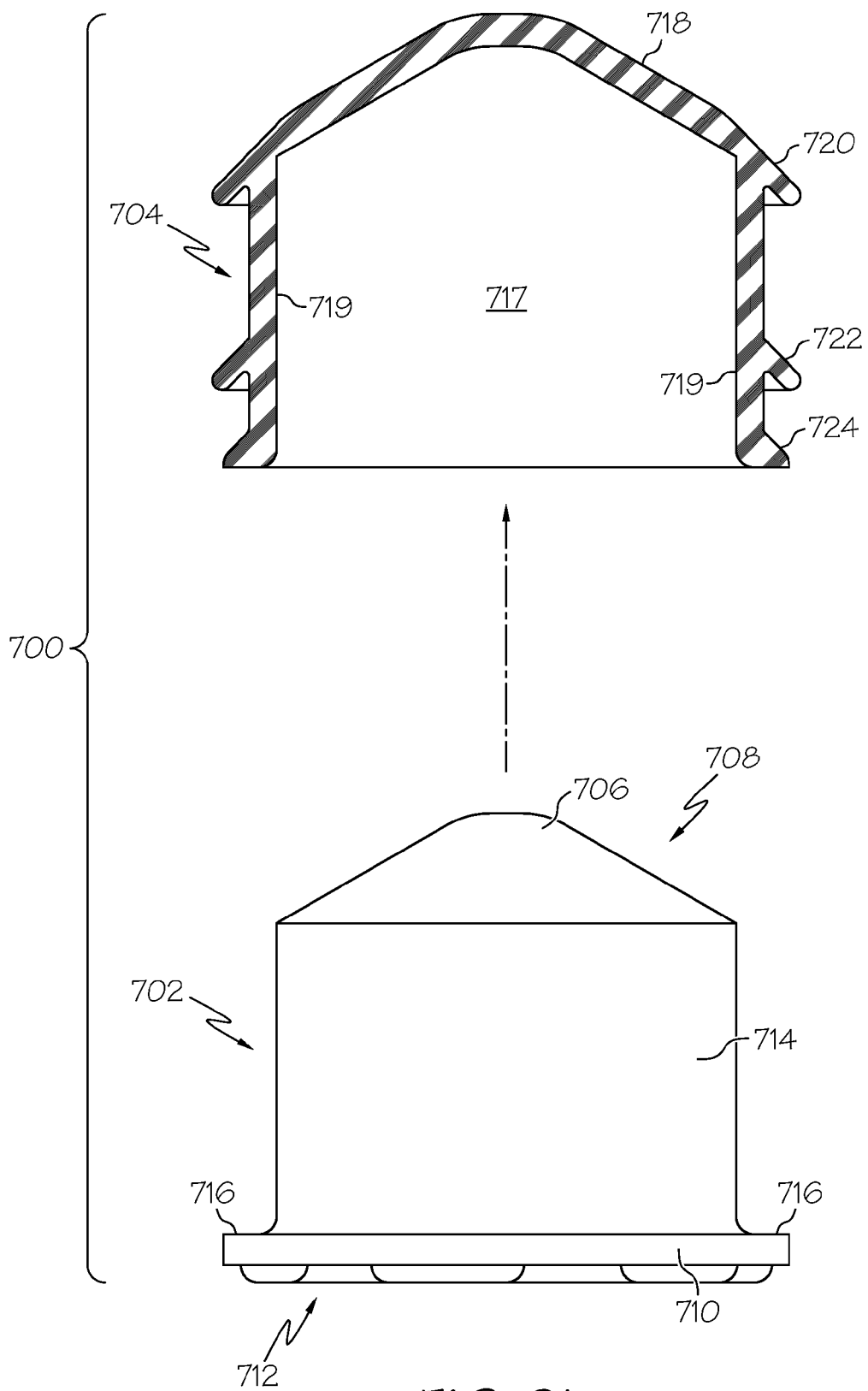
FIG. 21 is an assembly view of an exemplary embodiment of a syringe piston that utilizes a sealing cover.
Figure 22:
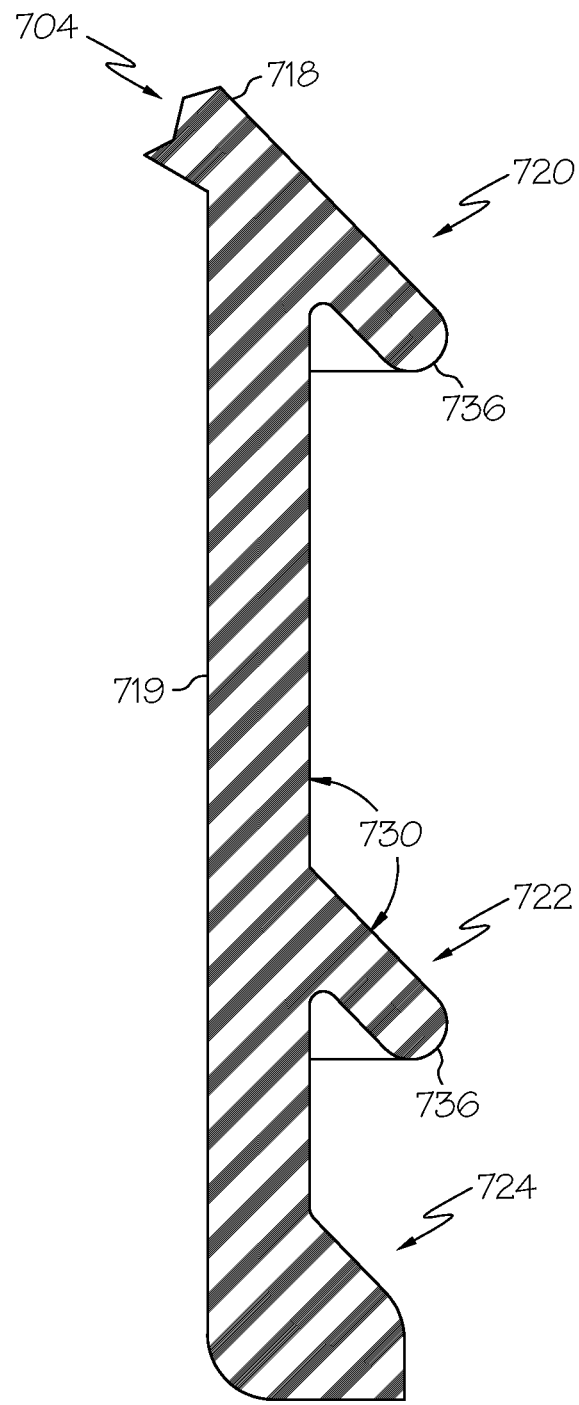
FIG. 22 is a cross-sectional detail view of various sealing features of the sealing cover shown in FIG. 21.

FIGS. 21 and 22 depict another exemplary embodiment of a syringe piston 700 that includes two primary components. FIG. 21 is an assembly view of the syringe piston 700, and FIG. 22 is a cross-sectional detail view of various sealing features of the syringe piston 700. It should be appreciated that an embodiment of the piston 700 might share some of the features, elements, and functionality described above for the syringe pistons that utilize check valves and/or that described above for the syringe pistons 500, 600. For the sake of brevity and clarity, common features and functionality will not be redundantly described in detail in the context of the piston 700.

The syringe piston 700 is similar to the syringe piston 600 (see FIGS. 18-20) in that it includes a piston body 702 and a resilient sealing component coupled to the piston body 702. In contrast to the configuration of the piston sealing sleeve 604 used with the piston 600, however, the piston 700 utilizes a piston sealing cover 704 that fits overlying at least a portion of the piston body 702.

In certain exemplary embodiments, the piston body 702 is fabricated as a one-piece molded component. Consistent with the previously described embodiments, the piston body 702 includes a tip 706 located at a fluid end 708, and a base 710 located at an actuator end 712. The base 710 is located opposite the tip 706, and the piston body 702 includes an outer seal-retaining surface 714 between the tip 706 and the base 710. Notably, the piston body 702 is similar in overall shape, structure, and functionality to the piston body 602 (FIG. 18). In this regard, the base 710 includes, defines, or is configured to serve as a retaining shoulder 716 for the piston sealing cover 704. Thus, when the syringe piston 700 is assembled, the bottom end of the piston sealing cover 704 may contact the base 710 in a manner similar to that shown in FIG. 19 for the syringe piston 600. The illustrated embodiment of the piston body 702, however, lacks any additional grooves, tongues, or other structural features designed to retain, position, or secure the piston sealing cover 704 on the piston body 702. It should be appreciated that alternate embodiments of the piston body 702 could implement such features if so desired.

The piston sealing cover 704 is preferably realized as a one-piece integrated component that is fabricated from a resilient material such as rubber, plastic, urethane, etc. The piston sealing cover 704 is shaped, sized, and configured in accordance with the dimensions and shape of the piston body 702. The piston sealing cover 704 may be conformally shaped in accordance with the piston body 702 to provide a compression fit overlying the tip 706 and the outer seal-retaining surface 714 when installed on the piston body 702. Depending on the particular implementation, the piston sealing cover 704 may be coupled to the piston body 702 with or without compressive force, and with or without an adhesive, a bonding agent, a welding compound, or the like.

The piston sealing cover 704 includes an interior cavity 717 defined therein. The interior cavity 717 is conformally shaped and sized to receive the tip 706 of the syringe piston 700 (as schematically represented by the diagram of FIG. 21). When the syringe piston 700 is assembled, the piston sealing cover 704 is coupled to the piston body 702 such that the piston sealing cover 704 overlies the tip 706 and surrounds at least a portion of the outer seal-retaining surface 714. In certain embodiments, the piston sealing cover 704 is designed to completely cover the tip 706 and to cover most if not all of the outer seal-retaining surface 714. In contrast, the piston sealing sleeve 604 of the syringe piston 600 (FIG. 19) leaves the fluid end 608 of the piston body 602 exposed.

Referring also to FIG. 22, the illustrated embodiment of the piston sealing cover 704 generally includes, without limitation: a cap portion 718; a sleeve portion 719 coupled to the cap portion 718; and three circumferential sealing elements formed on the sleeve portion 719 and configured to form an interference fluid seal with the interior wall of the corresponding syringe barrel (not shown). More specifically, the piston sealing cover 704 includes an upper fin-shaped fluid seal element 720, a lower fin-shaped fluid seal element 722, and an end seal element 724. As mentioned previously, more or less than three sealing elements could be employed in an embodiment of the piston sealing cover 704 if so desired.

The upper fin-shaped fluid seal element 720 is located at or near the transition between the cap portion 718 and the sleeve portion 719. When the syringe piston 700 is assembled, therefore, the upper fin-shaped fluid seal element 720 is positioned at or near the tip 706 of the piston body 702. The lower fin-shaped fluid seal element 722 is located between the upper fin-shaped fluid seal element 720 and the end seal element 724. When the syringe piston 700 is assembled, the end seal element 724 is located between the lower fin-shaped fluid seal element 722 and the base 710 of the piston body 702. As described above, the various features, elements, and structural components of the piston sealing cover 704 may be integrally formed with one another. Indeed, in preferred embodiments the piston sealing cover 704 is realized as a one-piece molded component that is fabricated from a resilient material.

The upper fin-shaped fluid seal element 720 and the lower fin-shaped fluid seal element 722 are shaped, sized, and configured in a similar manner. For example, these seal elements 720, 722 form an angle 730 (FIG. 22) with the outer sidewall of the sleeve portion 719. For this particular embodiment, the angle 730 is about 135 degrees, although different angles could be used to suit the needs of the specific application. Notably, each of the fluid seal elements 720, 722 has a constant cross-sectional width along the length dimension. In contrast, the piston sealing sleeve 604 of the syringe piston 600 employs tapered fin-shaped fluid seal elements 620, 622. In further contrast to the piston sealing sleeve 604, each of the fluid seal elements 720, 722 of the piston sealing cover 704 terminates at a rounded tip 736 having a defined radius. Of course, an alternate embodiment could employ tapered seal elements if so desired.

As described above for the other embodiments, each of the fluid seal elements 720, 722 exhibits asymmetric deflection characteristics that facilitate movement and gliding of the syringe piston 700 in the direction that corresponds to the delivery of medication fluid. Moreover, the upper fin-shaped fluid seal element 720 may be continuous with the cap portion 718 such that it forms a smooth transition with the cap portion 718. The end seal element 724 has a unique cross-sectional profile relative to the fluid seal elements 720, 722. As depicted in FIG. 22, the end seal element 724 does not extend outward as far as the fluid seal elements 720, 722. In addition, the end seal element 724 has more bulk than either of the fluid seal elements 720, 722, which may be desired for structural stability and rigidity.

The one-piece piston sealing cover 704 may be desirable to provide improved sealing when in contact with the medication fluid (relative to other embodiments that utilize a sleeve or a multiple-part sealing element. The piston sealing cover 704 may also provide a better barrier and sealing capability. Moreover, use of the piston sealing cover 704 may eliminate the need for over molding or bonding to the piston body 702, resulting in lower manufacturing cost and reduced assembly time.

It should be appreciated that the specific features and characteristics shown and described above for the various exemplary embodiments are neither exclusive nor required for any given embodiment. For example, any of the exemplary circumferential seal elements described above could be utilized with the syringe piston 500, the syringe piston 600, and/or the syringe piston 700 if so desired. As another example, retaining grooves, tongues, and/or other equivalent features could be utilized with the syringe piston 500 and/or the syringe piston 700 if so desired. Conversely, an alternate embodiment of the syringe piston 600 could be provided without retaining grooves and tongues. Thus, the individual features and elements shown and described may be implemented and deployed in an embodiment of a syringe piston as desired to suit the needs of the particular application.

While at least one exemplary embodiment has been presented in the foregoing detailed description, it should be appreciated that a vast number of variations exist. It should also be appreciated that the exemplary embodiment or embodiments described herein are not intended to limit the scope, applicability, or configuration of the claimed subject matter in any way. Rather, the foregoing detailed description will provide those skilled in the art with a convenient road map for implementing the described embodiment or embodiments. It should be understood that various changes can be made in the function and arrangement of elements without departing from the scope defined by the claims, which includes known equivalents and foreseeable equivalents at the time of filing this patent application.

What is claimed is:

1. A syringe piston comprising:
   a piston body having a tip, a base opposite the tip, and an outer seal-retaining surface between the tip and the base, the base including a retaining shoulder that extends outwardly from the base and the base defines a cavity;
   a piston sealing cover coupled to the piston body, the piston sealing cover overlying the tip and coupled around the outer seal-retaining surface, and the piston sealing cover comprising a fin-shaped fluid seal element to form an interference fluid seal with an interior wall of a syringe barrel, the fin-shaped fluid seal element located near the tip of the piston body and having a surface that faces the base of the piston body, the piston sealing cover including a circumferential end seal element that extends outwardly from the piston sealing cover, the circumferential end seal element spaced a distance apart from the fin-shaped fluid seal element along the piston sealing cover, and the piston sealing cover is coupled to the piston body such that the circumferential end seal element contacts the retaining shoulder of the base,
   wherein the surface is concave.

2. The syringe piston of claim 1, wherein the piston sealing cover is conformally shaped in accordance with the piston body to provide a compression fit overlying the tip and the outer seal-retaining surface.

3. The syringe piston of claim 1, wherein:
   the fin-shaped fluid seal element is located at the tip; and
   the piston sealing cover further comprises a second fin-shaped seal element located between the fin-shaped fluid seal element and the base.

4. The syringe piston of claim 1, wherein the fin-shaped fluid seal element is integrally formed with the piston sealing cover.

5. The syringe piston of claim 1, wherein the piston sealing cover is formed from a resilient material.

6. The syringe piston of claim 1, wherein the fin-shaped fluid seal element has asymmetric deflection characteristics.

7. The syringe piston of claim 6, wherein the fin-shaped fluid seal element has a tapered cross-sectional profile.

8. The syringe piston of claim 1, wherein:
   the piston body comprises an external circumferential groove formed therein;
   the piston sealing cover comprises an internal circumferential tongue formed thereon; and
   the internal circumferential tongue mates with the external circumferential groove to retain the piston sealing cover on the piston body.

9. The syringe piston of claim 1, wherein:
   the piston body comprises an external circumferential tongue formed thereon;
   the piston sealing cover comprises an internal circumferential groove formed therein; and
   the external circumferential tongue mates with the internal circumferential groove to retain the piston sealing cover on the piston body.

10. A fluid syringe comprising:
    a syringe barrel comprising an interior wall and a sealed main fluid chamber; and
    a syringe piston slidably coupled within the syringe barrel, the syringe piston comprising:
      a piston body having a tip, a base opposite the tip, and an outer seal-retaining surface between the tip and the base, the base including a retaining shoulder that extends outwardly from the base; and
      a piston sealing cover coupled to the piston body, the piston sealing cover completely covering the tip and overlying at least a portion of the outer seal-retaining surface, the piston sealing cover comprising a circumferential fluid seal element forming an interference fluid seal against the interior wall, the circumferential fluid seal element having asymmetric deflection characteristics and extending outwardly from a sleeve portion of the piston sealing cover for a first distance, and the piston sealing cover includes a circumferential end seal element that extends outwardly for a second distance, the second distance less that the first distance and the piston sealing cover is coupled to the piston body such that the circumferential end seal element contacts the retaining shoulder of the base.

11. The fluid syringe of claim 10, wherein the circumferential end seal element is located between the circumferential fluid seal element and the base of the piston body.

12. The fluid syringe of claim 11, wherein the circumferential end seal element has a tapered cross-sectional profile.

13. The fluid syringe of claim 10, wherein the piston sealing cover is conformally shaped in accordance with the piston body to provide a compression fit overlying the tip and the outer seal-retaining surface.

14. A sealing element for a syringe piston, the sealing element comprising:
   a cap portion;
   a sleeve portion coupled to the cap portion, the sleeve portion having a first end opposite a second end, with the first end coupled to the cap portion;
   an interior cavity defined by the cap portion and the sleeve portion, the interior cavity conformally shaped and sized to receive a tip of the syringe piston;
   a plurality of circumferential fin-shaped fluid seal elements formed on the sleeve portion to extend outwardly from the sleeve portion for a first distance, each of the plurality of circumferential fin-shaped fluid seal elements forming an interference fluid seal with an interior wall of a syringe barrel, with one of the plurality of circumferential fin-shaped fluid seal elements located at the first end and one of the plurality of circumferential fin-shaped fluid seal elements located between the first end and the second end; and
   a circumferential end seal element formed on the sleeve portion at the second end to extend outwardly from the sleeve portion for a second distance, the second distance different than the first distance.

15. The sealing element of claim 14, wherein the cap portion and the sleeve portion are integrally formed with one another.

16. The sealing element of claim 15, wherein the cap portion and the sleeve portion are conformally shaped to provide a compression fit on the syringe piston.

17. The sealing element of claim 15, wherein the cap portion and the sleeve portion are formed from a resilient material.

18. The sealing element of claim 14, wherein the plurality of circumferential fin-shaped fluid seal elements are integrally formed with the sleeve portion.

19. The sealing element of claim 14, wherein each of the circumferential fin-shaped fluid seal elements has asymmetric deflection characteristics.

20. The sealing element of claim 14, wherein each of the circumferential fin-shaped fluid seal elements has a tapered cross-sectional profile.

* * * * *